(12) United States Patent
Miller et al.

(10) Patent No.: US 8,986,325 B2
(45) Date of Patent: Mar. 24, 2015

(54) DEVICES, SYSTEMS, AND METHODS FOR CLOSING THE LEFT ATRIAL APPENDAGE

(75) Inventors: Gary H. Miller, Milpitas, CA (US); Russell A. Seiber, Redwood Shores, CA (US); Gregory W. Fung, San Mateo, CA (US)

(73) Assignee: SentreHEART, Inc., Redwood City, CA (US)

( * ) Notice: Subject to any disclaimer, the term of this patent is extended or adjusted under 35 U.S.C. 154(b) by 1280 days.

(21) Appl. No.: 12/363,381

(22) Filed: Jan. 30, 2009

(65) Prior Publication Data

US 2009/0143791 A1 Jun. 4, 2009

Related U.S. Application Data

(63) Continuation of application No. 12/055,213, filed on Mar. 25, 2008, now Pat. No. 8,771,297.

(60) Provisional application No. 60/921,002, filed on Mar. 30, 2007.

(51) Int. Cl.
*A61B 17/04* (2006.01)
*A61B 17/12* (2006.01)
*A61B 17/00* (2006.01)

(52) U.S. Cl.
CPC ... *A61B 17/12013* (2013.01); *A61B 2017/0477* (2013.01); *A61B 2017/0475* (2013.01);
(Continued)

(58) Field of Classification Search
CPC .................. A61B 17/12009; A61B 17/12013; A61B 17/12; A61B 2017/0477; A61B 2017/0475; A61B 2017/12009
USPC ......... 606/139, 113, 110, 111, 148, 140, 157; 600/127, 129; 604/509, 96.01, 97.01
See application file for complete search history.

(56) References Cited

U.S. PATENT DOCUMENTS 3,496,932 A 2/1970 Prisk at al.
3,677,597 A 7/1972 Stipek
(Continued)

FOREIGN PATENT DOCUMENTS

EP 0 598 219 A2 5/1994
EP 0 598 219 A3 5/1994
(Continued)

OTHER PUBLICATIONS

Blackshear, J.L. et al. (2003). "Thorascopic Extracardiac Obliteration of the Left Atrial Appendage for Stroke Risk Reduction in Atrial Fibrillation," *J. Am. Coll. Cardiol.* 42:1249-1252.
(Continued)

*Primary Examiner* — Gregory Anderson
*Assistant Examiner* — Christopher L Templeton
(74) *Attorney, Agent, or Firm* — Morrison & Foerster LLP

(57) ABSTRACT

Described here are devices, systems and methods for closing the left atrial appendage. Some of the methods described here utilize one or more guide members having alignment members to aid in positioning of a closure device. In general, these methods include advancing a first guide having a first alignment member into the left atrial appendage, advancing a second guide, having a second alignment member, into the pericardial space, aligning the first and second alignment members, advancing a left atrial appendage closure device into the pericardial space and adjacent to the left atrial appendage, and closing the left atrial appendage with the closure device. In these variations, the closure device typically has an elongate body having a proximal end and a distal end, and a closure element at least partially housed within the elongate body. The closure element comprises a loop defining a continuous aperture.

10 Claims, 19 Drawing Sheets

(52) U.S. Cl.
CPC . *A61B17/12009* (2013.01); *A61B 2017/00243* (2013.01); *A61B 2017/00867* (2013.01); *A61B 2017/00876* (2013.01)
USPC .......................... 606/139; 606/148; 606/157

(56) References Cited

U.S. PATENT DOCUMENTS

| | | | |
|---|---|---|---|
| 3,802,074 A | 4/1974 | Hoppe | |
| 3,841,685 A | 10/1974 | Kolodziej | |
| 3,999,555 A | 12/1976 | Person | |
| 4,018,229 A | 4/1977 | Komiya | |
| 4,030,509 A | 6/1977 | Heilman et al. | |
| 4,078,305 A | 3/1978 | Akiyama | |
| 4,181,123 A | 1/1980 | Crosby | |
| 4,249,536 A | 2/1981 | Vega | |
| 4,257,278 A | 3/1981 | Papadofrangakis et al. | |
| 4,319,562 A | 3/1982 | Crosby | |
| 4,596,530 A | 6/1986 | McGlinn | |
| 4,662,377 A | 5/1987 | Heilman et al. | |
| 4,765,341 A | 8/1988 | Mower et al. | |
| 4,817,608 A | 4/1989 | Shapland et al. | |
| 4,901,405 A | 2/1990 | Grover et al. | |
| 4,944,753 A | 7/1990 | Burgess et al. | |
| 4,991,578 A | 2/1991 | Cohen | |
| 4,991,603 A | 2/1991 | Cohen et al. | |
| 4,998,975 A | 3/1991 | Cohen et al. | |
| 5,033,477 A | 7/1991 | Chin et al. | |
| 5,108,406 A | 4/1992 | Lee | |
| 5,163,942 A | 11/1992 | Rydell | |
| 5,163,946 A | 11/1992 | Li | |
| 5,176,691 A | 1/1993 | Pierce | |
| 5,181,123 A | 1/1993 | Swank | |
| 5,226,535 A | 7/1993 | Rosdhy et al. | |
| 5,226,908 A | 7/1993 | Yoon | |
| 5,242,459 A | 9/1993 | Buelna | |
| 5,243,977 A | 9/1993 | Trabucco et al. | |
| 5,269,326 A | 12/1993 | Verrier | |
| 5,281,238 A | 1/1994 | Chin et al. | |
| 5,300,078 A | 4/1994 | Buelna | |
| 5,306,234 A | 4/1994 | Johnson | |
| 5,318,578 A | 6/1994 | Hasson | |
| 5,336,252 A | 8/1994 | Cohen | |
| 5,385,156 A | 1/1995 | Oliva | |
| 5,387,219 A | 2/1995 | Rappe | |
| 5,403,331 A | 4/1995 | Chesterfield et al. | |
| 5,405,351 A | 4/1995 | Kinet et al. | |
| 5,417,684 A | 5/1995 | Jackson et al. | |
| 5,423,821 A | 6/1995 | Pasque | |
| 5,423,830 A | 6/1995 | Schneebaum et al. | |
| 5,433,457 A | 7/1995 | Wright | |
| 5,433,730 A | 7/1995 | Alt | |
| 5,443,481 A | 8/1995 | Lee | |
| 5,449,367 A | 9/1995 | Kadry | |
| 5,494,240 A | 2/1996 | Waugh | |
| 5,498,228 A | 3/1996 | Royalty et al. | |
| 5,540,711 A | 7/1996 | Kieturakis et al. | |
| 5,571,161 A | 11/1996 | Starksen | |
| 5,591,177 A | 1/1997 | Lehrer | |
| 5,609,597 A | 3/1997 | Lehrer | |
| 5,624,430 A | 4/1997 | Eton et al. | |
| 5,624,453 A | 4/1997 | Ahmed | |
| 5,634,895 A | 6/1997 | Igo et al. | |
| 5,676,162 A | 10/1997 | Larson, Jr. et al. | |
| 5,676,651 A | 10/1997 | Larson, Jr. et al. | |
| 5,678,547 A | 10/1997 | Faupel et al. | |
| 5,681,278 A | 10/1997 | Igo et al. | |
| 5,682,906 A | 11/1997 | Sterman et al. | |
| 5,683,364 A | 11/1997 | Zadini et al. | |
| 5,683,445 A | 11/1997 | Swoyer | |
| 5,693,059 A | 12/1997 | Yoon | |
| 5,693,091 A | 12/1997 | Larson, Jr. et al. | |
| 5,699,748 A | 12/1997 | Linskey, Jr. et al. | |
| 5,702,430 A | 12/1997 | Larson, Jr. et al. | |
| 5,707,336 A | 1/1998 | Rubin | |
| 5,716,367 A | 2/1998 | Koike et al. | |
| 5,716,392 A | 2/1998 | Bourgeois et al. | |
| 5,727,569 A | 3/1998 | Benetti et al. | |
| 5,728,151 A | 3/1998 | Garrison et al. | |
| 5,735,877 A | 4/1998 | Pagedas | |
| 5,741,281 A | 4/1998 | Martin | |
| 5,752,526 A | 5/1998 | Cosgrove | |
| 5,766,151 A * | 6/1998 | Valley et al. | 604/103.07 |
| 5,766,216 A | 6/1998 | Gangal et al. | |
| 5,766,217 A | 6/1998 | Christy | |
| 5,769,863 A | 6/1998 | Garrison | |
| 5,779,727 A | 7/1998 | Orejola | |
| 5,792,151 A | 8/1998 | Heck et al. | |
| 5,797,870 A | 8/1998 | March et al. | |
| 5,797,929 A | 8/1998 | Andreas et al. | |
| 5,797,946 A | 8/1998 | Chin | |
| 5,799,661 A | 9/1998 | Boyd et al. | |
| 5,810,845 A | 9/1998 | Yoon | |
| 5,823,946 A | 10/1998 | Chin | |
| 5,827,216 A | 10/1998 | Igo et al. | |
| 5,840,059 A | 11/1998 | March et al. | |
| 5,855,586 A | 1/1999 | Habara et al. | |
| 5,865,791 A | 2/1999 | Whayne et al. | |
| 5,871,531 A | 2/1999 | Struble | |
| 5,873,876 A | 2/1999 | Christy | |
| 5,879,375 A | 3/1999 | Larson, Jr. et al. | |
| 5,882,299 A | 3/1999 | Rastegar et al. | |
| 5,895,298 A | 4/1999 | Faupel et al. | |
| 5,897,586 A | 4/1999 | Molina | |
| 5,900,433 A | 5/1999 | Igo et al. | |
| 5,906,620 A | 5/1999 | Nakao et al. | |
| 5,908,429 A | 6/1999 | Yoon | |
| 5,908,435 A | 6/1999 | Samuels | |
| 5,910,124 A | 6/1999 | Rubin | |
| 5,910,129 A | 6/1999 | Koblish et al. | |
| 5,921,994 A | 7/1999 | Andreas et al. | |
| 5,924,424 A | 7/1999 | Stevens et al. | |
| RE36,269 E | 8/1999 | Wright | |
| 5,941,819 A | 8/1999 | Chin | |
| 5,961,440 A | 10/1999 | Schweich, Jr. et al. | |
| 5,964,699 A | 10/1999 | Rullo et al. | |
| 5,968,010 A | 10/1999 | Waxman et al. | |
| 5,972,013 A | 10/1999 | Schmidt | |
| 5,984,866 A | 11/1999 | Rullo et al. | |
| 5,984,917 A | 11/1999 | Fleischman et al. | |
| 5,991,668 A | 11/1999 | Leinders et al. | |
| 5,997,525 A | 12/1999 | March et al. | |
| 6,006,122 A | 12/1999 | Smits | |
| 6,010,531 A | 1/2000 | Donlon et al. | |
| 6,015,382 A | 1/2000 | Zwart et al. | |
| 6,045,570 A | 4/2000 | Epstein et al. | |
| 6,048,329 A | 4/2000 | Thompson et al. | |
| 6,059,750 A | 5/2000 | Fogarty et al. | |
| 6,067,942 A | 5/2000 | Fernandez | |
| 6,071,281 A | 6/2000 | Burnside et al. | |
| 6,081,738 A | 6/2000 | Hinohara et al. | |
| 6,083,153 A | 7/2000 | Rullo et al. | |
| 6,090,042 A | 7/2000 | Rullo et al. | |
| 6,095,968 A | 8/2000 | Snyders | |
| 6,110,170 A | 8/2000 | Taylor et al. | |
| 6,120,431 A | 9/2000 | Magovern et al. | |
| 6,132,438 A | 10/2000 | Fleischman et al. | |
| 6,148,230 A | 11/2000 | KenKnight | |
| 6,149,595 A | 11/2000 | Seitz et al. | |
| 6,152,144 A | 11/2000 | Lesh et al. | |
| 6,152,920 A | 11/2000 | Thompson et al. | |
| 6,152,936 A | 11/2000 | Christy et al. | |
| 6,155,968 A | 12/2000 | Wilk | |
| 6,157,852 A | 12/2000 | Selmon et al. | |
| 6,161,543 A | 12/2000 | Cox et al. | |
| 6,162,195 A | 12/2000 | Igo et al. | |
| 6,167,889 B1 | 1/2001 | Benetti | |
| 6,199,556 B1 | 3/2001 | Benetti et al. | |
| 6,200,303 B1 | 3/2001 | Verrior et al. | |
| 6,206,004 B1 | 3/2001 | Schmidt et al. | |
| 6,224,584 B1 | 5/2001 | March et al. | |
| 6,231,518 B1 | 5/2001 | Grabek et al. | |
| 6,237,605 B1 | 5/2001 | Vaska et al. | |
| 6,241,667 B1 | 6/2001 | Vetter et al. | |
| 6,258,021 B1 | 7/2001 | Wilk | |

(56) References Cited

U.S. PATENT DOCUMENTS

| | | |
|---|---|---|
| 6,266,550 B1 | 7/2001 | Selmon et al. |
| 6,280,415 B1 | 8/2001 | Johnson |
| 6,283,127 B1 | 9/2001 | Sterman et al. |
| 6,290,674 B1 | 9/2001 | Roue et al. |
| 6,293,906 B1 | 9/2001 | Vanden Hoek et al. |
| 6,296,630 B1 | 10/2001 | Altman et al. |
| 6,311,692 B1 | 11/2001 | Vaska et al. |
| 6,311,693 B1 | 11/2001 | Sterman et al. |
| 6,314,962 B1 | 11/2001 | Vaska et al. |
| 6,314,963 B1 | 11/2001 | Vaska et al. |
| 6,319,201 B1 | 11/2001 | Wilk |
| 6,333,347 B1 | 12/2001 | Hunter et al. |
| 6,346,074 B1 | 2/2002 | Roth |
| 6,379,366 B1 | 4/2002 | Fleischman et al. |
| 6,423,051 B1 | 7/2002 | Kaplan et al. |
| 6,474,340 B1 | 11/2002 | Vaska et al. |
| 6,485,407 B2 | 11/2002 | Alferness et al. |
| 6,488,689 B1 | 12/2002 | Kaplan et al. |
| 6,494,211 B1 | 12/2002 | Boyd et al. |
| 6,551,303 B1 | 4/2003 | Van Tassel et al. |
| 6,561,969 B2 | 5/2003 | Frazier et al. |
| 6,592,552 B1 | 7/2003 | Schmidt |
| 6,610,055 B1 | 8/2003 | Swanson et al. |
| 6,610,072 B1 | 8/2003 | Christy et al. |
| 6,613,062 B1 | 9/2003 | Leckrone et al. |
| 6,632,229 B1 | 10/2003 | Yamanouchi |
| 6,652,555 B1 | 11/2003 | Van Tassel et al. |
| 6,656,175 B2 | 12/2003 | Francischelli et al. |
| 6,666,861 B1 | 12/2003 | Grabek |
| 6,692,491 B1 | 2/2004 | Phan |
| 6,733,509 B2 | 5/2004 | Nobles et al. |
| 6,736,774 B2 | 5/2004 | Benetti et al. |
| 6,755,338 B2 | 6/2004 | Hahnen et al. |
| 6,786,898 B2 | 9/2004 | Guenst |
| 6,789,509 B1 | 9/2004 | Motsinger |
| 6,830,174 B2 | 12/2004 | Hillstead et al. |
| 6,830,576 B2 | 12/2004 | Fleischman et al. |
| 6,985,776 B2 | 1/2006 | Kane et al. |
| 7,011,671 B2 | 3/2006 | Welch |
| 7,041,111 B2 | 5/2006 | Chu |
| 7,056,294 B2 | 6/2006 | Khairkhahan et al. |
| 7,063,682 B1 | 6/2006 | Whayne et al. |
| 7,063,693 B2 | 6/2006 | Guenst |
| 7,175,619 B2 | 2/2007 | Koblish et al. |
| 7,186,214 B2 | 3/2007 | Ness |
| 7,207,988 B2 | 4/2007 | Leckrone et al. |
| 7,226,440 B2 | 6/2007 | Gelfand et al. |
| 7,226,458 B2 | 6/2007 | Kaplan et al. |
| 7,264,587 B2 | 9/2007 | Chin |
| 7,294,115 B1 | 11/2007 | Wilk |
| 7,297,144 B2 | 11/2007 | Fleischman et al. |
| 7,309,328 B2 | 12/2007 | Kaplan et al. |
| 7,318,829 B2 | 1/2008 | Kaplan et al. |
| 7,326,221 B2 | 2/2008 | Sakamoto et al. |
| 7,331,979 B2 | 2/2008 | Khosravi et al. |
| 7,608,091 B2 | 10/2009 | Goldfarb et al. |
| 7,722,641 B2 | 5/2010 | van der Burg et al. |
| 7,828,810 B2 | 11/2010 | Liddicoat et al. |
| 7,846,168 B2 | 12/2010 | Liddicoat et al. |
| 7,905,900 B2 | 3/2011 | Palermo et al. |
| 7,918,865 B2 | 4/2011 | Liddicoat et al. |
| 8,157,818 B2 | 4/2012 | Gartner et al. |
| 8,469,983 B2 | 6/2013 | Fung et al. |
| 8,636,767 B2 | 1/2014 | McClain |
| 2001/0025132 A1 | 9/2001 | Alferness et al. |
| 2002/0017306 A1 | 2/2002 | Cox et al. |
| 2002/0022860 A1 | 2/2002 | Borillo et al. |
| 2002/0049457 A1 | 4/2002 | Kaplan et al. |
| 2002/0058925 A1 | 5/2002 | Kaplan et al. |
| 2002/0062136 A1 | 5/2002 | Hillstead et al. |
| 2002/0068970 A1 | 6/2002 | Cox et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111636 A1 | 8/2002 | Fleischman et al. |
| 2002/0111637 A1 | 8/2002 | Kaplan et al. |
| 2003/0014049 A1 | 1/2003 | Koblish et al. |
| 2003/0024537 A1 | 2/2003 | Cox et al. |
| 2003/0045900 A1 | 3/2003 | Hahnen et al. |
| 2003/0069577 A1 | 4/2003 | Vaska et al. |
| 2003/0083542 A1 | 5/2003 | Alferness et al. |
| 2003/0083674 A1 | 5/2003 | Gibbens, III |
| 2003/0109863 A1 | 6/2003 | Francischelli et al. |
| 2003/0120264 A1 | 6/2003 | Lattouf |
| 2003/0158464 A1 | 8/2003 | Bertolero |
| 2003/0181942 A1 | 9/2003 | Sutton et al. |
| 2003/0187460 A1 | 10/2003 | Chin et al. |
| 2003/0236535 A1 | 12/2003 | Onuki et al. |
| 2004/0030335 A1 | 2/2004 | Zenati et al. |
| 2004/0034347 A1 | 2/2004 | Hall et al. |
| 2004/0044361 A1 | 3/2004 | Frazier et al. |
| 2004/0049210 A1 | 3/2004 | VanTassel et al. |
| 2004/0059352 A1 | 3/2004 | Burbank et al. |
| 2004/0064138 A1 | 4/2004 | Grabek |
| 2004/0078069 A1 | 4/2004 | Francischelli et al. |
| 2004/0102804 A1 | 5/2004 | Chin |
| 2004/0106918 A1 | 6/2004 | Cox et al. |
| 2004/0111101 A1 | 6/2004 | Chin |
| 2004/0116943 A1 | 6/2004 | Brandt et al. |
| 2004/0162579 A1 | 8/2004 | Foerster |
| 2004/0225212 A1 | 11/2004 | Okerlund et al. |
| 2004/0225300 A1 | 11/2004 | Goldfarb et al. |
| 2004/0243176 A1 | 12/2004 | Hahnen et al. |
| 2004/0260273 A1 | 12/2004 | Wan |
| 2005/0033280 A1 | 2/2005 | Francischelli et al. |
| 2005/0033287 A1 | 2/2005 | Sra |
| 2005/0033321 A1 | 2/2005 | Fleischman et al. |
| 2005/0043745 A1 | 2/2005 | Alferness et al. |
| 2005/0085843 A1 | 4/2005 | Opolski et al. |
| 2005/0107824 A1 | 5/2005 | Hillstead et al. |
| 2005/0149068 A1 | 7/2005 | Williams et al. |
| 2005/0149069 A1 | 7/2005 | Bertolero et al. |
| 2005/0154376 A1 | 7/2005 | Riviere et al. |
| 2005/0154404 A1 | 7/2005 | Liddicoat |
| 2005/0165466 A1 | 7/2005 | Morris et al. |
| 2005/0256532 A1 | 11/2005 | Nayak et al. |
| 2006/0004323 A1* | 1/2006 | Chang et al. ............ 604/28 |
| 2006/0004388 A1 | 1/2006 | Whayne et al. |
| 2006/0009715 A1 | 1/2006 | Khairkhahan et al. |
| 2006/0020162 A1 | 1/2006 | Whayne et al. |
| 2006/0020271 A1 | 1/2006 | Stewart et al. |
| 2006/0020336 A1 | 1/2006 | Liddicoat |
| 2006/0034930 A1 | 2/2006 | Khosravi et al. |
| 2006/0100545 A1 | 5/2006 | Ayala et al. |
| 2006/0200169 A1 | 9/2006 | Sniffin |
| 2006/0212045 A1 | 9/2006 | Schilling et al. |
| 2006/0247672 A1 | 11/2006 | Vidlund et al. |
| 2006/0253128 A1 | 11/2006 | Sekine et al. |
| 2006/0253129 A1 | 11/2006 | Liddicoat et al. |
| 2007/0016228 A1 | 1/2007 | Salas |
| 2007/0027456 A1 | 2/2007 | Gartner et al. |
| 2007/0060951 A1 | 3/2007 | Shannon |
| 2007/0073313 A1 | 3/2007 | Liddicoat et al. |
| 2007/0083082 A1 | 4/2007 | Kiser et al. |
| 2007/0083225 A1 | 4/2007 | Kiser et al. |
| 2007/0083232 A1 | 4/2007 | Lee |
| 2007/0088369 A1 | 4/2007 | Shaw et al. |
| 2007/0100405 A1 | 5/2007 | Thompson et al. |
| 2007/0135822 A1 | 6/2007 | Onuki et al. |
| 2007/0149988 A1 | 6/2007 | Michler et al. |
| 2007/0179345 A1 | 8/2007 | Santilli |
| 2007/0249991 A1 | 10/2007 | Whayne et al. |
| 2007/0260278 A1 | 11/2007 | Wheeler et al. |
| 2007/0270637 A1 | 11/2007 | Takemoto et al. |
| 2007/0270891 A1 | 11/2007 | McGuckin, Jr. |
| 2008/0009843 A1 | 1/2008 | de la Torre |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0097489 A1 | 4/2008 | Goldfarb et al. |
| 2008/0147097 A1 | 6/2008 | Liddicoat et al. |
| 2008/0221593 A1 | 9/2008 | Liddicoat et al. |
| 2008/0228265 A1 | 9/2008 | Spence et al. |
| 2008/0243183 A1 | 10/2008 | Miller et al. |

(56) References Cited

U.S. PATENT DOCUMENTS

| | | |
|---|---|---|
| 2008/0294174 A1 | 11/2008 | Bardsley et al. |
| 2008/0294175 A1 | 11/2008 | Bardsley et al. |
| 2008/0312664 A1 | 12/2008 | Bardsley et al. |
| 2009/0043317 A1 | 2/2009 | Cavanaugh et al. |
| 2009/0082797 A1 | 3/2009 | Fung et al. |
| 2009/0157118 A1 | 6/2009 | Miller et al. |
| 2010/0069925 A1 | 3/2010 | Friedman et al. |
| 2010/0174296 A1 | 7/2010 | Vakharia et al. |
| 2011/0087247 A1 | 4/2011 | Fung et al. |
| 2011/0144660 A1 | 6/2011 | Liddicoat et al. |
| 2013/0144311 A1 | 6/2013 | Fung et al. |

FOREIGN PATENT DOCUMENTS

| | | |
|---|---|---|
| EP | 0 598 219 B1 | 5/1994 |
| EP | 1 010 397 A1 | 11/1999 |
| GB | 1 506 142 A | 4/1978 |
| JP | 7-296645 A2 | 11/1995 |
| JP | 7-299073 A | 11/1995 |
| JP | 11-507262 A | 6/1999 |
| JP | 2001-120560 A | 5/2001 |
| JP | 2002-540901 A | 12/2002 |
| JP | 2005-110860 A | 4/2005 |
| JP | 2005-296645 A | 10/2005 |
| JP | 2005-531360 A | 10/2005 |
| JP | 2007-504886 A | 3/2007 |
| WO | WO-94/01045 A1 | 1/1994 |
| WO | WO-94/04079 A1 | 3/1994 |
| WO | WO-94/08514 A1 | 4/1994 |
| WO | WO-96/40356 A1 | 12/1996 |
| WO | WO-97/11644 A1 | 4/1997 |
| WO | WO-97/43957 A1 | 11/1997 |
| WO | WO-00/61202 A1 | 10/2000 |
| WO | WO-2004/002327 A1 | 1/2004 |
| WO | WO-2004/066828 A2 | 8/2004 |
| WO | WO-2004/066828 A3 | 8/2004 |
| WO | WO-2005/034767 A1 | 4/2005 |
| WO | WO-2005/034767 C2 | 4/2005 |
| WO | WO-2005/034802 A2 | 4/2005 |
| WO | WO-2005/034802 A3 | 4/2005 |
| WO | WO-2006/110734 A2 | 10/2006 |
| WO | WO-2006/115689 A1 | 11/2006 |
| WO | WO-2007/056502 A1 | 5/2007 |
| WO | WO-2008/017080 A2 | 2/2008 |
| WO | WO-2008/017080 A3 | 2/2008 |
| WO | WO-2008/017080 C2 | 2/2008 |
| WO | WO-2008/036408 A2 | 3/2008 |
| WO | WO-2008/036408 A3 | 3/2008 |
| WO | WO-2008/091612 A2 | 7/2008 |
| WO | WO-2008/091612 A3 | 7/2008 |
| WO | WO-2008/121278 A2 | 10/2008 |
| WO | WO-2009/039191 A2 | 3/2009 |
| WO | WO-2009/094237 A1 | 7/2009 |
| WO | WO-2010/006061 A2 | 1/2010 |
| WO | WO-2010/006061 A3 | 1/2010 |
| WO | WO-2010/048141 A2 | 4/2010 |
| WO | WO-2010/048141 A3 | 4/2010 |
| WO | WO-2010/115030 A1 | 10/2010 |

OTHER PUBLICATIONS

Cox, J.L. et al. (1991). "The Surgical Treatment of Atrial Fibrillation IV. Surgical Technique," *J. Thorac. Cardiovasc. Surg.* 101 (4):584-592.

Cox, J.L. et al. (Aug. 1995). "Modification of the MAZE Procedure for Atrial Flutter and Atrial Fibrillation I. Rationale and Surgical Results," *J. Thorac. Cardiovasc. Surg.* 110(2):473-484.

Cox, J.L. et al. (Aug. 1995). "Modification of the MAZE Procedure for Atrial Flutter and Atrial Fibrillation II. Surgical Technique of the Maze III Procedure," *J. Thorac. Cardiovasc. Surg.* 110(2):485-495.

Cox, J.L. et al. (Nov. 1999). "Impact of the MAZE Procedure on the Stroke Rate in Patients with Atrial Fibrillation," *J. Thorac. Cardiovasc. Surg.* 118:833-840.

Dullum, M.K.C. et al. (1999). "Xyphoid MIDCAB: Report of the Technique and Experience with a Less Invasive MIDCAB Procedure," *Heart Surgery Forum* 2(1):77-81.

International Search Report mailed on Feb. 27, 2007, for PCT Application No. PCT/US2008/003938, filed on Mar. 25, 2008, 2 pages.

Kim, K.B. et al. (Jan. 1998). "Effect of the Cox Maze Procedure on the Secretion of Atrial Natriuretic Peptide," *J. Thorac. Cardiovasc. Surf.* 115(1):139-46; discussion 146-147.

Macris, M. et al. (Jan. 1999). "Minimally Invasive Access of the Normal of the Normal Pericardium: Initial Clinical Experience with a Novel Device," *Clin. Cardiol.* 22(Suppl. I):I-36-I-39.

Morris, J.J. Jr. (1997). "Transvenous Versus Transthoracic Cardiac Pacing," Chapter 16 in *Cardiac Pacing* pp. 239-245.

Naclerio, et al. (1997). "Surgical Techniques for Permanent Ventricular Pacing," Chapter 10 in *Cardiac Pacing* pp. 145-168.

Non-Final Office Action mailed on Mar. 13, 2008 for U.S. Appl. No. 10/963,371, filed Oct. 11, 2004, 13 pages.

Non-Final Office Action mailed on Aug. 6, 2008 for U.S. Appl. No. 10/963,371, filed Oct. 11, 2004, 14 pages.

Odell, J.A. et al. (1996). "Thorascopic Obliteration of the Left Atrial Appendage: Potential for Stroke Reduction?" *Ann. Thorac. Surg.* 61:565-569.

Seferovic, P. et al. (Jan. 1999). "Initial Clinical Experience with the Perducer Device: Promising New Tool in the Diagnosis and Treatment of Pericardial Disease," *Clin. Cardiol.* 22(Supp I.):I-30-I-35.

Sosa, E. et al. (1996). "A New Technique to Perform Epicardial Mapping in the EP Laboratory," *J. Cardiovasc. Electrophysiol.* 7(6):531-536.

Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.

Sosa, E. et al. (Dec. 14, 1999). "Different Ways of Approaching the Normal Pericardial Space," *Circulation* 100(24):e115-e116.

Stewart, S. (1974). "Placement of the Sutureless Epicardial Pacemaker Lead by the Subxiphoid Approach," *Ann. of Thoracic Surg.* 18(3):308-131.

Stokes, K. (Jun. 1990). "Implantable Pacing Lead Technology," *IEEE Engineering in Medicine and Biology* pp. 43-49.

Suehiro, S. et al. (1996). "Echocardiography-Guided Pericardiocentesis With a Needle Attached to a Probe," *Ann. Thoracic Surg.* 61:741-742.

U.S. Appl. No. 12/363,359, filed Jan. 30, 2009, for Miller et al.

Watkins, L. et al. (Nov. 1982). "Implantation of the Automatic Defibrillator: The Subxiphoid Approach," *Ann. of Thoracic Surg.* 34(5):514-520.

Written Opinion of the International Searching Authority mailed on Feb. 27, 2007, for PCT Application No. PCT/US2008/003938, filed on Mar. 25, 2008, 10 pages.

Final Office Action mailed on Jun. 22, 2009, for U.S. Appl. No. 10/963,371, filed Oct. 11, 2004, 11 pages.

Non-Final Office Action mailed on Jun. 26, 2009, for U.S. Appl. No. 11/600,671, filed Nov. 15, 2006, 9 pages.

Final Office Action mailed on Apr. 14, 2010, for U.S. Appl. No. 11/600,671, filed Nov. 15, 2006, 7 pages.

Final Office Action mailed on Jul. 21, 2010, for U.S. Appl. No. 11/400,714, filed Apr. 7, 2006, 10 pages.

Non-Final Office Action mailed on Dec. 30, 2009, for U.S. Appl. No. 11/400,714, filed Apr. 7, 2006, 8 pages.

Non-Final Office Action mailed on Jul. 22, 2010, for U.S. Appl. No. 12/037,802, filed Feb. 26, 2008, 10 pages.

Notice of Allowance mailed on Sep. 17, 2010, for U.S. Appl. No. 10/963,371, filed Oct. 11, 2004, 7 pages.

Notice of Allowance mailed on Sep. 17, 2010, for U.S. Appl. No. 11/600,671, filed Nov. 15, 2006, 7 pages.

European Office Action mailed on Sep. 16, 2010, for European Patent Application No. 08727155.7, filed on Mar. 25, 2008, 5 pages.

Afibfacts.com (Date Unknown). "Cox-Maze III: The Gold Standard Treatment for Atrial Fibrillation: Developing a Surgical Option for Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation >, last visited on Apr. 20, 2007, 4 pages.

(56) References Cited

OTHER PUBLICATIONS

Al-Saady, N.M. et al. (1999). "Left Atrial Appendage: Structure, Function, and Role in Thromboembolism," *Heart* 82:547-554.

Albers, G.W. (Jul. 11, 1994). "Atrial Fibrillation and Stroke: Three New Studies, Three Remaining Questions," *Arch Intern Med* 154:1443-1448.

Alonso, M. et al. (Mar. 4, 2003). "Complications With Femoral Access in Cardiac Catheterization. Impact of Previous Systematic Femoral Angiography and Hemostasis With VasoSeal-Es® Collagen Plug," *Rev. Esp. Cardiol.* 56(6):569-577.

Aronow, W.S. et al. (Apr. 2009). "Atrial Fibrillation: The New Epidemic of the Ageing World," *Journal of Atrial Fibrillation* 1(6):337-361.

Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.

Bath, P.M.W. et al. (2005). "Current Status of Stroke Prevention in Patients with Atrial Fibrillation," *European Heart Journal Supplements* 7(Supplement C):C12-C18.

Benjamin, B.A. et al. (1994). "Effect of Bilateral Atrial Appendectomy on Postprandial Sodium Excretion in Conscious Monkeys," *Society for Experimental Biology and Medicine* 2006: 1 page.

Beygui, F. et al. (2005, e-pub. Oct. 21, 2005). "Multimodality Imaging of Percutaneous Closure of the Left Atrial Appendage," *Clinical Vignette*, 1 page.

Bisleri, G. et al. (Jun. 3, 2005). "Innovative Monolateral Approach for Closed-Chest Atrial Fibrillation Surgery," *The Annals of Thoracic Surgery* 80:e22-e25.

Björk, V.O. et al. (Aug. 1961). "Sequelae of Left Ventricular Puncture with Angiocardiography," *Circulation* 24:204-212.

Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.

Bonanomi, G. et al. (Jan. 1, 2003). "Left Atrial Appendectomy and Maze," *Journal of the American College of Cardiology* 41(1):169-171.

Bonow, R.O. et al. (1998) "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Journal of the American Heart Association* 98:1949-1984.

Botham, R.J. et al. (1959). "Pericardial Tamponade Following Percutaneous Left Ventricular Puncture," *Circulation* 19:741-744.

Brock, R. et al. (1956). "Percutaneous Left Ventricular Puncture in the Assessment of Aortic Stenosis," *Thorax* 11:163-171.

Burke, R.P. et al. (1992). "Improved Surgical Approach to Left Atrial Appendage Aneurysm," *Journal of Cardiac Surgery* 7(2):104-107.

Canaccord Adams (Aug. 11, 2008). "A-Fib: Near A Tipping Point," 167 pages.

Chung, M.K. (Jul. 2003). "Current Clinical Issues in Atrial Fibrillation," *Cleveland Clinic Journal of Medicine* 70(Supp. 3):S6-S11.

Coffin, L.H. (Jun. 1985). "Use of the Surgical Stapler to Obliterate the Left Atrial Appendage," *Surgery, Gynecology & Obstetric* 160:565-566.

Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.

Costa, R. et al. (2006). "Bi-Atrial Subxiphoid Epicardial Pacemaker in Superior Vena Cava Syndrome," *Arq. Bras. Cardiol.* 87:e45-e47.

Cox, J.L. et al. (2004). "The Role of Surgical Intervention in the Management of Atrial Fibrillation," *Texas Heart Institute Journal* 31(3):257-265.

Crystal, E. et al. (2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.

D'Avila, A. et al. (Apr. 2003). "Pericardial Anatomy for the Interventional Electrophysiologist," *Journal of Cardiovascular Electrophysiology* 14(4):422-430.

D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.

Demaria, A.N. et al. (Dec. 17, 2003). "Highlights of the Year JACC 2003," *Journal of the American College of Cardiology* 42(12):2156-2166.

Deneu, S, et al. (Jul. 11, 1999). "Catheter Entrapment by Atrial Suture During Minimally Invasive Port-access Cardiac Surgery," *Canadian Journal of Anesthesia* 45(10):983-986.

Deponti, R. et al. (Mar. 7, 2006). "Trans-Septal Catheterization in the Electrophysiology Laboratory: Data From a Multicenter Survey Spanning 12 Years," *Journal of the American College of Cardiology* 45(5):1037-1042.

Donal, E. et al. (Sep. 2005). "The Left Artrial Appendage, a Small, Blind-Ended Structure: A Review of Its Echocardiographic Evaluation and Its Clinical Role," *Chest* 128(3):1853-1862.

Donnino, R. et al. (2007). "Left Atrial Appendage Thrombus Outside of a 'Successful' Ligation," *European Journal of Echocardiography* pp. 1-2.

Feinberg, W.M. et al. (Mar. 13, 1995). "Prevalence, Age Distribution, and Gender of Patients With Atrial Fibrillation," *Arch Intern Med* 155:469-473.

Fieguth, H.G. et al. (1997). "Inhibition of Atrial Fibrillation by Pulmonary Vein Isolation and Auricular Resection—Experimental Study in A Sheep Model," *European Journal of Cardio-Thoracic Surgery* 11:714-721.

Fisher, D.C. et al. (Dec. 1998). "Large Gradient Across a Partially Ligated Left Atrial Appendage," *Journal of the American Society of Echocardiography* 11(12):1163-1165.

Friberg, L. et al. (2006). "Stroke Prophylaxis in Atrial Fibrillation: Who Gets it and Who Does Not?" *European Heart Journal* 27:1954-1964.

Friedman, P.A. et al. (Aug. 2009). "Percutaneous Epicardial Left Atrial Appendage Closure: Preliminary Results of an Electrogram Guided Approach," *Journal of Cardiovascular Electrophysiology* 29(8):908-915.

Fuster, V. et al. (2001). "ACC/AHA/ESC Guidelines for the Management of Patients with Atrial Fibrillation," *European Heart Journal* 22:1852-1923.

Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.

Gardiner, G.A. Jr. et al. (Apr. 1986). "Complications of Transluminal Angioplasty," *Radiology* 159:201-208.

Gillinov, A.M. (2007). "Advances in Surgical Treatment of Atrial Fibrillation," *Journal of the American Heart Association* 38(part 2):618-623.

Gilman, R.A. et al. (Apr. 1963). "Direct Left Ventricular Puncture," *California Medicine* 98(4):200-203.

Goodwin, W.E. et al. (Nov. 1950). "Translumbar Aortic Puncture and Retrograde Catheterization of the Aorta in Aortography and Renal Arteriography," *Annals of Surgery* 132(5):944-958.

Gottlieb. L.K. et al. (Sep. 12, 1994). "Anticoagulation in Atrial Fibrillation," *Arch Intern Med.* 154:1945-1953.

Graffigna, A. et al. (1993). "Surgical Treatment of Wolff-Parkinson-White Syndrome: Epicardial Approach Without the Use of Cardiopulmonary Bypass," *J. Card. Surg.* 8:108-116.

Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.

Halperin, J.L. et al. (Aug. 1988). "Atrial Fibrillation and Stroke: New Ideas, Persisting Dilemmas," *Journal of the American Heart Association* 19(8):937-941.

Halperin, J.L. et al. (2003). "Obliteration of the Left Atrial Appendage for Prevention of Thromboembolism," *Journal of the American College of Cardiology* 42(7):1259-1261.

(56) References Cited

OTHER PUBLICATIONS

Hammill, S.C. (May 2006). "Epicardial Ablation: Reducing the Risks," *J. Cardiovasc. Electrophysiol.* 17:550-552.

Hara, H. et al. (Jan. 2008). "Percutaneous Left Atrial Appendage Obliteration," *JACC: Cardiovascular Imagin* 1(1):92-93.

Hart, R.G. et al. (1999). "Atrial Fibrillation and Thromboembolism: A Decade of Progress in Stroke Prevention," *Annals of Internal Medicine* 131(9):688-695.

Hart, R.G. et al. (2001). "Atrial Fibrillation and Stroke: Concepts and Controversies," *Stroke* 32:803-808.

Hart, R.G. (Sep. 11, 2003). "Atrial Fibrillation and Stroke Prevention," *The New England Journal of Medicine* 349(11):1015-1016.

Healey, J.S. et al. (Oct. 2003). "Surgical Closure of the Left Atrial Appendage for the Prevention of Stroke: A Randomized Pilot Trial of Safety and Efficacy (The Left Atrial Appendage Occlusion Study—LAAOS)," presented at The Canadian Cardiovascular Congress 2003, Toronot, Canada, Abstract No. 666, 2 pages.

Healey, J.S. et al. (2005). "Left Atrial Appendage Occlusion Study (LAAOS): Results of a Randomized Controlled Pilot Study of Left Atrial Appendage Occlusion During Coronary Bypass Surgery in Patients at Risk for Stroke," *Surgery* 150(2):288-293.

Hein, R. et al. (2005). "Patent Foramen Ovale and Left Atrial Appendage: New Devices and Methods for Closure," *Pediatric Cardiology* 26(3):234-240.

Heist, E.K. et al. (Nov. 2006). "Analysis of the Left Atrial Appendage by Magnetic Resonance Angiography in Patients with Atrial Fibrillation," *Heart Rhythm* 3(11):1313-1318.

Ho, I. et al. (Apr. 24, 2007). "Percutaneous Epicardial Mapping Ablation of a Posteroseptal Accessory Pathway," *Circulation* 115:418-421.

Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.

Hoit, B.D. et al. (Jan. 1993). "Altered Left Atrial Compliance After Atrial Appendectomy. Influence on Left Atrial and Ventricular Filling," *Circulation Research* 72(1):167-175.

Inoue, Y. et al. (Jul.-Aug. 1997). "Video Assisted Thoracoscopic and Cardioscopic Radiofrequency Maze Ablation," *Asaio Journal* 43(4):334-337, Abstract Only.

Jais, P. et al. (2003). "Radiofrequency Ablation for Atrial Fibrillation," *European Society of Cardiology* 5(Supplement H):H34-H39.

Johnson, W.D. et al. (2000). "The Left Appendage: Our Most Lethal Human Attachment! Surgical Implications," *Euro. J. Cardiothoracic. Surg.* 17:718-722.

Jongbloed, M.R.M. et al. (2005). "Clinical Applications of Intracardiac Echocardiography in Interventional Procedures," *Heart* 91:981-990.

Kamohara, K. et al. (2006). "Evaluation of a Novel Device for Left Atrial Appendage Exclusion: The Second-generation Atrial Exclusion Device," *The Journal of Thoracic and Cardiovascular Surgery* 132(2):340-346.

Kanderian, A.S. et al. (2008). "Success of Surgical Left Atrial Appendage Closure: Assessment by Transesophageal Echocardiography," *Journal of the American College of Cardiology* 52(11):924-929.

Kato, H. et al. (Aug. 1, 1996). "Evaluation of Left Atrial Appendage Stasis in Patients With Atrial Fibrillation Using Transesophagel Echocardiography With an Intravenous Albumin-Contrast Agent," *The American Journal of Cardiology* 78:365-369.

Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.

Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.

Kerut, E.K. et al. (2008). "Anatomy of the Left Atrial Appendage," *Echocardiography* 25(6):669-673.

Khargi, K. et al. (2005). "Surgical Treatment of Atrial Fibrillation: A Systematic Review," *European Journal of Cardiothoracic Surgery* 27:258-265.

Kistler, P.M. et al. (May 2007). "The Left Atrial Appendage: Not Just an Innocent Bystander," *J. Cardiovasc Electrophysiol* 18(5):465-466.

Klein, H. et al. (Apr. 1990). "The Implantable Automatic Cardioverter-Defibrillator," *Herz* 15(2):111-125, Abstract Only.

Kolb, C. et al. (Feb. 2004). "Incidence of Antitachycardia Therapy Suspension Due to Magnet Reversion in Implantable Cardioverter Defibrillators," *Pace* 27:221-223.

Krikorian, J.G. et al. (Nov. 1978). "Pericardiocentesis," *Am. J. Med.* 65(5):808-814.

Krum, D. et al. (2004). "Visualization of Remnants of the left Atrial Appendage Following Epicardial Surgical Removal," *Heart Rhythm* 1:249.

Lacomis, J.M. et al. (Oct. 2003). "Multi-Detector Row CT of the Left Atrium and Pulmonary Veins before Radio-frequency Catheter Ablation for Atrial Fibrillation," *Radio Graphics* 23:S35-S48.

Lacomis, J.M. et al. (2007, e-pub. Oct. 17, 2007). "Dynamic Multidimensional Imaging of the Human Left Atrial Appendage," *Eurospace Advance Access* 9:1134-1140.

Lee, R. et al. (1999). "The Closed Heart MAZE: A Nonbypass Surgical Technique," *The Annals of Thoracic Surgery* 67:1696-1702.

Levinson, M.L. et al. (1998). "Minimally Invasive Atrial Septal Defect Closure Using the Subxyphoid Approach," *Heart Surg. Forum* 1(1):49-53, Abstract Only.

Lewis, D.R. et al. (1999). "Vascular Surgical Intervention for Complications of Cardiovascular Radiology: 13 Years' Experience in a Single Centre," *Ann. R. Coll. Surg. Engl.* 81:23-26.

Li, H. (2007). "Magnet Decoration, Beautiful But Potentially Dangerous for Patients with Implantable Pacemakers or Defibrillators," *Heart Rhythm* 4(1):5-6.

Lindsay, B.D. (1996). "Obliteration of the Left Atrial Appendage: A Concept Worth Testing," *The Annals of Thoracic Surgery* 51:515.

Lip, G.Y.H. et al. (Jun. 2001). "Thromboprophylaxis for Atrial Flutter," *European Heart Journal* 22(12):984-987.

Lustgarten, D.L. et al. "Cryothermal Ablation: Mechanism of Tissue Injury and Current Experience in the Treatment of Tachyarrhythmias," *Progress in Cardiovascular Diseases* 41(6):481-498.

Maisch, B. et al. (Jan. 1999). "Intrapreicardial Treatment of Inflammatory and Neoplastic Pericarditis Guided by Pericardioscopy and Epicardial Biopsy-Results from a Pilot Study," *Clin. Cardiol.* 22(Supp. I):I-17-I-22.

Mannam, A.P. et al. (Apr. 1, 2002). "Safety of Subxyphoid Pericardial Access Using a Blunt-Tip Needle," *The American Journal of Cardiology* 89:891-893.

Mattox, K.L. et al. (May 1997). "Newer Diagnostic Measure and Emergency Management," *Ches Surg Clin N Am.* 7(2):213-216, Abstract Only.

McCarthy, P.M. et al. (2008). "Epicardial Atrial Fibrillation Ablation," Chapter 23 in *Contemporary Cardiology: Atrial Fibrillation, From Bench to Bedside*, Natale, A. et al. eds., Humana Press: Totowa, NJ, pp. 323-332.

McCaughan, J.J. Jr., et al. (2009). "Aortography Utilizing Percutaneous Left Ventricular Puncture," located at <http://www.archsurg.com>, last visited on Apr. 7, 2009, pp. 746-751.

McClelland, R.R. (1978). "Congenital Aneurysmal Dilatation of the Left Auricle Demonstrated by Sequential Cardiac Blood-Pool Scintiscanning," *J. Nucl. Med.* 19(5):507-509.

Melo, J. et al. (Apr. 21, 2008). "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.

Miller, P.S.J. et al. (Feb. 2005). "Are Cost Benefits of Anticoagulation for Stroke Prevention in Atrial Fibrillation Underestimated?" *Stroke* 366:360-366.

Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Epidemiology* 114:119-125.

(56) References Cited

OTHER PUBLICATIONS

Mráz, T. et al. (Apr. 2007). "Role of Echocardiography in Percutaneous Occlusion of the left Atrial Appendage," *Echocardiography* 24(4):401-404.
Nakai, T. et al. (May 7, 2002). "Percutaneous Left Atrial Appendage Occlusion (PLAATO) for Preventing Cardioembolism: First Experience in Canine Model," *Circulation* 105:2217-2222.
Nakajima, H. et al. (2004). "Consequence of Atrial Fibrillation and Risk of Embolism After Percutaneous Mitral Commissurotomy: The Necessity of the Maze Procedure," *The Annals of Thoracic Surgery* 78:800-806.
O'Donnell, M. et al. (2005). "Emerging Therapies for Stroke Prevention in Atrial Fibrillation," *European Heart Journal* 7(Supplement C):C19-C27.
Omran, H. et al. (1997). "Left Atrial Appendage Function in Patients with Atrial Flutter," *Heart* 78:250-254.
Onalan, O. et al. (2005). "Nonpharmacologic Stroke Prevention in Atrial Fibrillation," *Expert Rev. Cardiovasc. Ther.* 3(4):619-633.
Onalan, O. et al. (2007). "Left Atrial Appendage Exclusion for Stroke Prevention in Patients With Nonrheumatic Atrial Fibrillation," *Stroke* 38(part 2):624-630.
Ostermayer, S. et al. (2003). "Percutaneous Closure of the Left Atrial Appendage," *Journal of Interventional Cardiology* 16(6):553-556.
Ota, T. et al. (2006). "Epicardial Atrial Ablation Using a Novel Articulated Robotic Medical Probe Via a Percutaneous Subxiphoid Approach," *National Institute of Health* 1(6):335-340.
Ota, T. et al. (Oct. 2007). "Impact of Beating Heart left Atrial Ablation on Left-sided Heart Mechanics," *The Journal of Thoracic and Cardiovascular Surgery* 134:982-988.
Pennec, P-Y. et al. (2003). "Assessment of Different Procedures for Surgical Left Atrial Appendage Exclusion," *The Annals of Thoracic Surgery* 76:2167-2168.
Perk, G. et al. (Aug. 2009). "Use of Real Time Three-Dimensional Transesophageal Echocardiography in Intracardiac Catheter Based Interventions," *J. Am Soc Echocardiogr* 22(8):865-882.
Pollick C. (Feb. 2000). "Left Atrial Appendage Myopathy," *Chest* 117(2):297-308.
Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.
Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.
Robicsek, F. (1987). "Closed-Chest Decannulation of Transthoracically Inserted Aortic Balloon Catheter without Grafting," *Journal of Cardiac Surgery* 2(2):327-329.
Ross, J. Jr. et al. (Jun. 3, 2008). "Transseptal Left Heart Catheterization: a 50-Year Odyssey," *Journal of the American College of Cardiology* 51(22):2107-2115.
Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.
Ruchat, P. et al. (2002). "Off-pump Epicardial Compartmentalization for Ablation of Atrial Fibrillation," *Interactive Cardio Vascular and Thoracic Surgery* 1:55-57.
Salzberg, S.P. et al. (2008). "Surgical Left Atrial Appendage Occlusion: Evaluation of a Novel Device with Magnetic Resonance Imaging," *European Journal of Cardiothoracic Surgery* 34:766-770.
Sapp, J. et al. (Dec. 2001). "Electrophysiology and Anatomic Characterization of an Epicardial Accessory Pathway," *Journal of Cardiovascular Electrophysiology* 12(12):1411-1414.
Scharf, C. et al. (2005). "Catheter Ablation for Atrial Fibrillation: Pathophysiology, Techniques, Results and Current Indications," *Continuous Medical Education* 8:53-61.
Scherr, D. et al. (Apr. 2009). "Incidence and Predictors of left Atrial Thrombus Prior to Catheter Ablation of Atrial Fibrillation," *Journal of Cardiovascular Electrophysiology* 20(4):379-384.

Schmidt, H. et at. (2001). "Prevalence of Left Atrial Chamber and Appendage Thrombi in Patients With Atrial Flutter and Its Clinical Significance," *Journal of the American College of Cardiology* 38(3):778-784.
Schneider, B. et al. (2005). "Surgical Closure of the Left Atrial Appendage—A Beneficial Procedure?" *Cardiology* 104:124-132.
Schweikert, R.A. et al. (Sep. 16, 2003). "Percutaneous Pericardial Instrumentation for Endo-Epicardial Mapping of Previously Failed Ablation," *Circulation* 108:1329-1335.
Schweikert, R.A. et al. (2005). "Epicardial Access: Present and Future Applications for Interventional Electrophysiologists," Chapter 25 in *New Arrhythmia Technolgies*, Wang, P.J. ed., Blackwell Publishing, pp. 242-256.
Sengupta, P.P. et al. (2005). "Transoesophageal Echocardiography," *Heart* 91:541-547.
Sharada, K. et al. (2005). "Non-Surgical Transpericardial Catheter Ablation of Post-Infarction Ventricular Tachycardia," *Indian Heart J* 57:58-61.
Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.
Singer, D.E. et al. (Sep. 2004). "Antithrombotic Therapy in Atrial Fibrillation: The Seventh ACCP Conference on Antithrombotic and Thrombolytic Therapy," *Chest* 126(3):429-456.
Smith, P.W. (Nov. 1956). "Diagnosis of Mitral Regurgitation by Cardioangiography," *Circulation* 14:847-853.
Soejima, K. et al. (2004). "Subxiphoid Surgical Approach for Epicardial Catheter-Based Mapping and Ablation in Patients With Prior Cardiac Surgery or Difficult Pericardial Access," *Circulation* 110:1197-1201.
Sosa, E. et al. (Jul. 15, 2002). "Gaining Access to the Pericardial Space," *The American Journal of Cardiology* 90:203-204.
Sosa, E. et al. (Apr. 2005). "Epicardial Mapping and Ablation Techniques to Control Centricular Tachycardia," *Techniques and Technology* 16(4):449-452.
Sparks, P.B. et al. (2001). "Is Atrial Flutter a Risk Factor for Stroke?" *Journal of the American College of Cardiology* 38(3):785-788.
Spodick, D.H. (Nov. 1970). "Medical History of the Pericardium," *The American Journal of Cardiology* 26:447-454.
Stewart, J.M. et al. (Apr. 1992). "Bilateral Atrial Appendectomy Abolishes Increased Plasma Atrial Natriuretic Peptide Release and Blunts Sodium and Water Excretion During Volume Loading in Conscious Dogs," *Circulation Research* 70(4):724-732.
Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.
Stollberger, C. et al. (2000). "Is the Left Atrial Appendage Our Most Lethal Attachment?" *European Journal of Cardio-Thoracic Surgery* 18:625-626.
Stollberger, C. et al. (Dec. 2003). "Elimination of the Left Atrial Appendage to Prevent Stroke or Embolism?: Anatomic, Physiologic, and Pathophysiologic Considerations," 124(6):2356-2362.
Stollberger, C. et al. (2006). "Stroke Prevention by Means of Epicardial Occlusion of the Left Atrial Appendage," *Journal of Thoracic and Cardiovascular Surgery* 132(1):207-208.
Stollberger, C. et al. (2007). "Arguments Against Left Atrial Appendage occlusion for Stroke Prevention," *Stroke* 38: 1 page.
Stollberger, C. et al. (2007). "Leave the Left Atrial Appendage Untouched for Stroke Prevention!" *Journal of Thoracic and Cardiovascular Surgery* 134(2):549-550.
Su, P. et al. (Sep. 2008, e-pub. May 8, 2007). "Occluding the Left Atrial Appendage: Anatomical Consideration," *Heart* 94(9):1166-1170.
Subramanian, V.A. (Jun. 1997). "Less Invasive Arterial CABG on a Beating Heart," *Ann Thorac. Surg.* 63(6 Suppl.):S68-S71.
Subramanian, V.A. et al. (Dec. 1997). "Minimally Invasive Direct Coronary Artery Bypass Grafting: two-Year Clinical Experience," *Ann. Thorac. Surg.* 64(6):1648-1653, Abstract Only.
Sun, F. et al. (Feb. 2006). "Subxiphoid Access to Normal Pericardium with Micropuncture Set: Technical Feasibility Study in Pigs," *Radiology* 238(2):719-724.

(56) References Cited

OTHER PUBLICATIONS

Szili-Torok, T. et al. (2001). "Transseptal Left heart Catheterisation Guided by Intracardiac Echocardiography," *Heart* 86:e11-e15.
Tabata, T. et al. (Feb. 1, 2998). "Role of Left Atrial Appendage in left Atrial Reservoir Function as Evaluated by Left Atrial Appendage Clamping During Cardiac Surgery," *The American Journal of Cardiology* 81:327-332.
Tomar, M. et al. (Jul.-Aug. 2006). "Transcatheter Closure of Fossa Ovalis Atrial Septal Defect: A Single Insitutional Experience," *Indian Heart Journal* 58(4): 325-329.
Troughton, R.W. et al. (Feb. 28, 2004). "Pericarditis," *The Lancet* 363:717-727.
Ulicny K.S. et al. (Jun. 1992). "Conjoined Subrectus Pocket for Permanent Pacemaker Placement in the Neonate," *Ann. Thorac Surg.* 53(6):1130-1131, Abstract Only.
Valderrabano, M. et al. (Sep. 2004). "Percutaneous Epicardial Mapping During Ablation of Difficult Accessory Pathways as an Alternative to Cardiac Surgery," *Heart Rhythm* 1(3):311-316.
Von Korn, H. et al. (2006). "Simultaneous Combined Interventional Percutaneous Left Atrial Auricle and Atrial Septal Defect Closure," *Heart* 92:1462.
Wang, T.J. et al. (Aug. 27, 2003). "A Risk Score for Predicting Stroke or Death in Individuals With new-Onset Atrial Fibrillation in the Community," *American Medical Association* 290(8):1049-1056.
W.L. Gore & Associates (Aug. 11, 2006). "Gore Helex™ Septal Occluder," located at <http://www.fda.gov/cdrh/pdf5/p050006a.pdf>, last visited on Jun. 14, 2007, 3 pages.
Wolber, T. et al. (Jan. 2007). "Potential Interference of Small Neodymium Magnets with Cardiac pacemakers and Implantable Cardioverter-defibrillators," *Heart Rhythm* 4(1):1-4.
Wolf, P.A. et al. (Oct. 1978). "Epidemiologic Assessment of Chronic Atrial Fibrillation and Risk of Stroke: The Fiamingham Study," *Neurology* 28:973-977.
Wolf, P.A. et al. (1991). "Atrial Fibrillation as an Independent Risk Factor for Stroke: The Framingham Study," *Journal of the American Heart Association* 22(8):983-988.
Wolf, P.A. et al. (Feb. 1998). "Impact of Atrial Fibrillation on Mortality, Stroke, and Medical Costs," *Arch Intern Med* 158:229-234.
Wong, J.W.W. et al. (2006). "Impact of Maze and Concomitant Mitral Valve Surgery on Clinical Outcomes," *The Annals of Thoracic Surgery* 82:1938-1947.
Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.
Wood, M.A. (Jan. 2006). "Percutaneous Pericardial Instrumentation in the Electrophysiology Laboratory: A Case of Need," *Heart Rhythm* 3(1):11-12.
Wudel, J.H. et al. (Apr. 3, 2008). "Video-Assisted Epicardial Ablation and left Atrial Appendage Exclusion for Atrial Fibrillation: Extended Follow-Up," *The Annals of Thoracic Surgery* 85:34-38.
Wyse, D.G. et al. (Dec. 5, 2002). "Of 'Left Atrial Appendage Amputation, Ligation, or Occlusion in Patients with Atrial Fibrillation'," *N. Engl J Med* 347(23):1825-1833, Abstract Only.
Yamada, Y. et al. (Aug. 2006). "Video-Assisted Thoracoscopy to Treat Atrial Tachycardia Arising from Left Atrial Appendage," *Journal of Cardiovascular Electrophysiology* 17(8):895-898.
Zapolanski, A. et al. (May 2008). "Safe and Complete Exclusion of the left Atrial Appendage, A Simple Epicardial Approach," *Innovations* 3(3):161-163.
Zenati, M.A. et al. (Sep. 2003). "Left Heart Pacing Lead Implantation Using Subxiphoid Videopericardioscopy," *Journal of Cardiovascular Electrophysiology* 14(9):949-953.
Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.
Zenati, M.A. et al. (2005). "Modification of the Left Atrial Appendage," Chapter 12 in *Innovative Management of Atrial Fibrillation*, Schwartzman, David ed., Blackwell Science Ltd., 5 pages.
Final Office Action mailed on Apr. 26, 2011, for U.S. Appl. No. 12/037,802, filed Feb. 26, 2008, 9 pages.
Final Office Action mailed on Sep. 20, 2011, for U.S. Appl. No. 12/212,511, filed Sep. 17, 2008, 8 pages.
Final Office Action mailed on Oct. 28, 2011, for U.S. Appl. No. 12/055,213, filed Mar. 25, 2008, 15 pages.
International Preliminary Report on Patentability mailed on Oct. 15, 2009, for PCT Application No. PCT/US2008/003938, filed on Mar. 25, 2008, 7 pages.
Non-Final Office Action mailed on Nov. 15, 2010, for U.S. Appl. No. 12/055,213, filed Mar. 25, 2008, 18 pages.
Non-Final Office Action mailed on Feb. 17, 2011, for U.S. Appl. No. 12/212,511, filed Sep. 17, 2008, 14 pages.
Non-Final Office Action mailed on Apr. 28, 2011, for U.S. Appl. No. 12/055,213, filed Mar. 25, 2008, 20 pages.
Non-Final Office Action mailed on Oct. 27, 2011, for U.S. Appl. No. 12/363,359, filed Jan. 30, 2009, 11 pages.
Non-Final Office Action mailed on Dec. 22, 2011, for U.S. Appl. No. 13/033,532, filed Feb. 23, 2011, 8 pages.
Notice of Allowance mailed on Nov. 24, 2010, for U.S. Appl. No. 11/400,714, filed Apr. 7, 2006, 8 pages.
Final Office Action mailed on May 4, 2012, for U.S. Appl. No. 12/363,359, filed Jan. 30, 2009, 10 pages.
Final Office Action mailed on Jul. 11, 2012, for U.S. Appl. No. 13/033,532, filed Feb. 23, 2011, 8 pages.
Final Office Action mailed on Jul. 24, 2012, for U.S. Appl. No. 12/212,511, filed Sep. 17, 2008, 6 pages.
Final Office Action mailed on Oct. 18, 2012, for U.S. Appl. No. 12/124,023, filed May 20, 2008, 15 pages.
Non-Final Office Action mailed on Mar. 7, 2012, for U.S. Appl. No. 12/124,023, filed May 20, 2008, 13 pages.
Non-Final Office Action mailed on Apr. 2, 2012, for U.S. Appl. No. 12/212,511, filed Sep. 17, 2008, 5 pages.
Non-Final Office Action mailed on Jun. 17, 2014, for U.S. Appl. No. 12/363,359, filed Jan. 30, 2009, 7 pages.
Canadian Office Action mailed on Apr. 16, 2014 for Canadian Patent Application No. 2,682,398, filed on Mar. 25, 2008, 4 pages.
Final Office Action mailed on Nov. 8, 2013, for U.S. Appl. No. 12/037,802, filed Feb. 26, 2008, 15 pages.
Final Office Action mailed on Jan. 13, 2014, for U.S. Appl. No. 12/752,873, filed Apr. 1, 2010, 10 pages.
Non-Final Office Action mailed on Sep. 18, 2013, for U.S. Appl. No. 12/055,213, filed Mar. 25, 2008, 15 pages.
Non-Final Office Action mailed on May 31, 2013, for U.S. Appl. No. 12/124,023, filed May 20, 2008, 14 pages.
Non-Final Office Action mailed on Apr. 2, 2014, for U.S. Appl. No. 13/033,532, filed Feb. 23, 2011, 8 pages.
Notice of Allowance mailed on Feb. 22, 2013, for U.S. Appl. No. 12/212,511, filed Sep. 17, 2008, 8 pages.
Notice of Allowance mailed on Mar. 18, 2013, for U.S. Appl. No. 12/212,511, filed Sep. 17, 2008, 6 pages.
Notice of Allowance mailed on Mar. 4, 2014, for U.S. Appl. No. 12/055,213, filed Mar. 25, 2008, 9 pages.
Notice of Allowance mailed on Apr. 3, 2014, for U.S. Appl. No. 12/037,802, filed Feb. 26, 2008, 8 pages.
Notice of Allowance mailed on Feb. 18, 2014, for Australian Patent Application No. 2008233242, filed on Mar. 25, 2008, 2 pages.

* cited by examiner

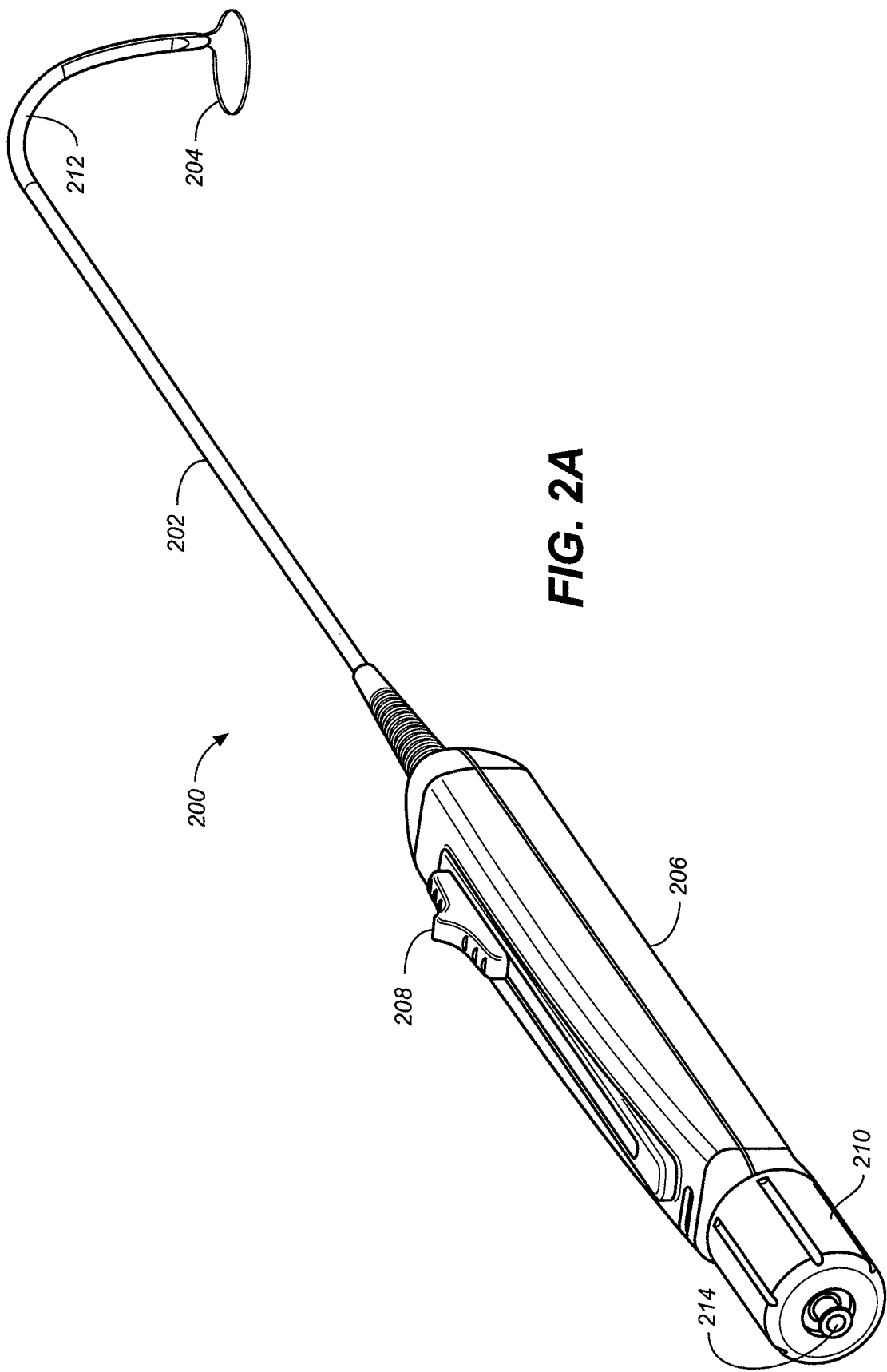

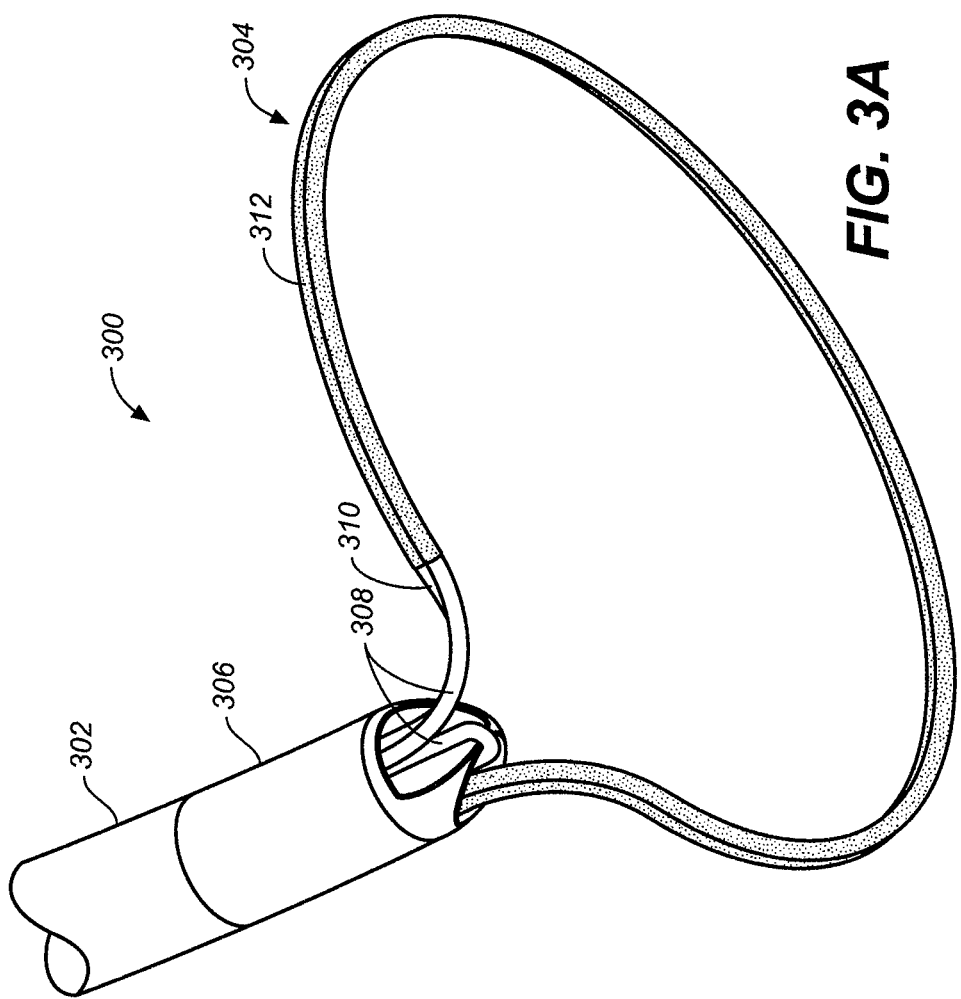

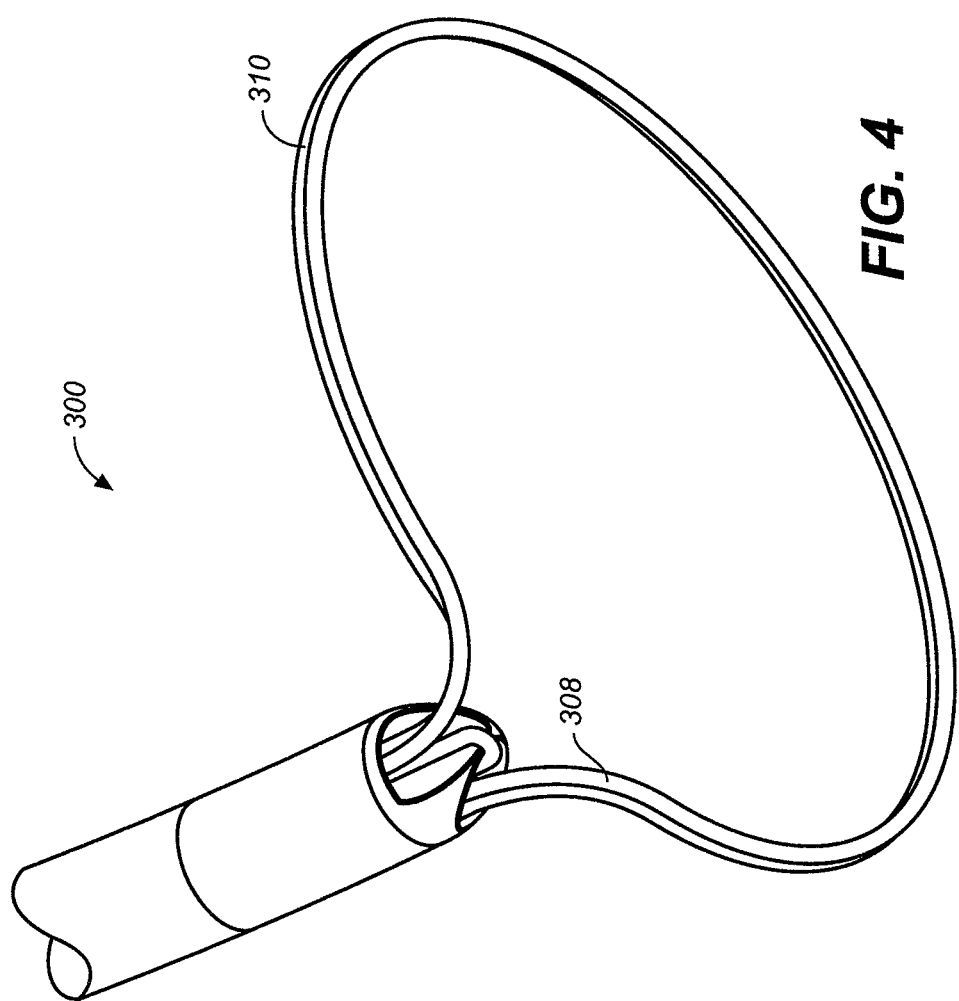

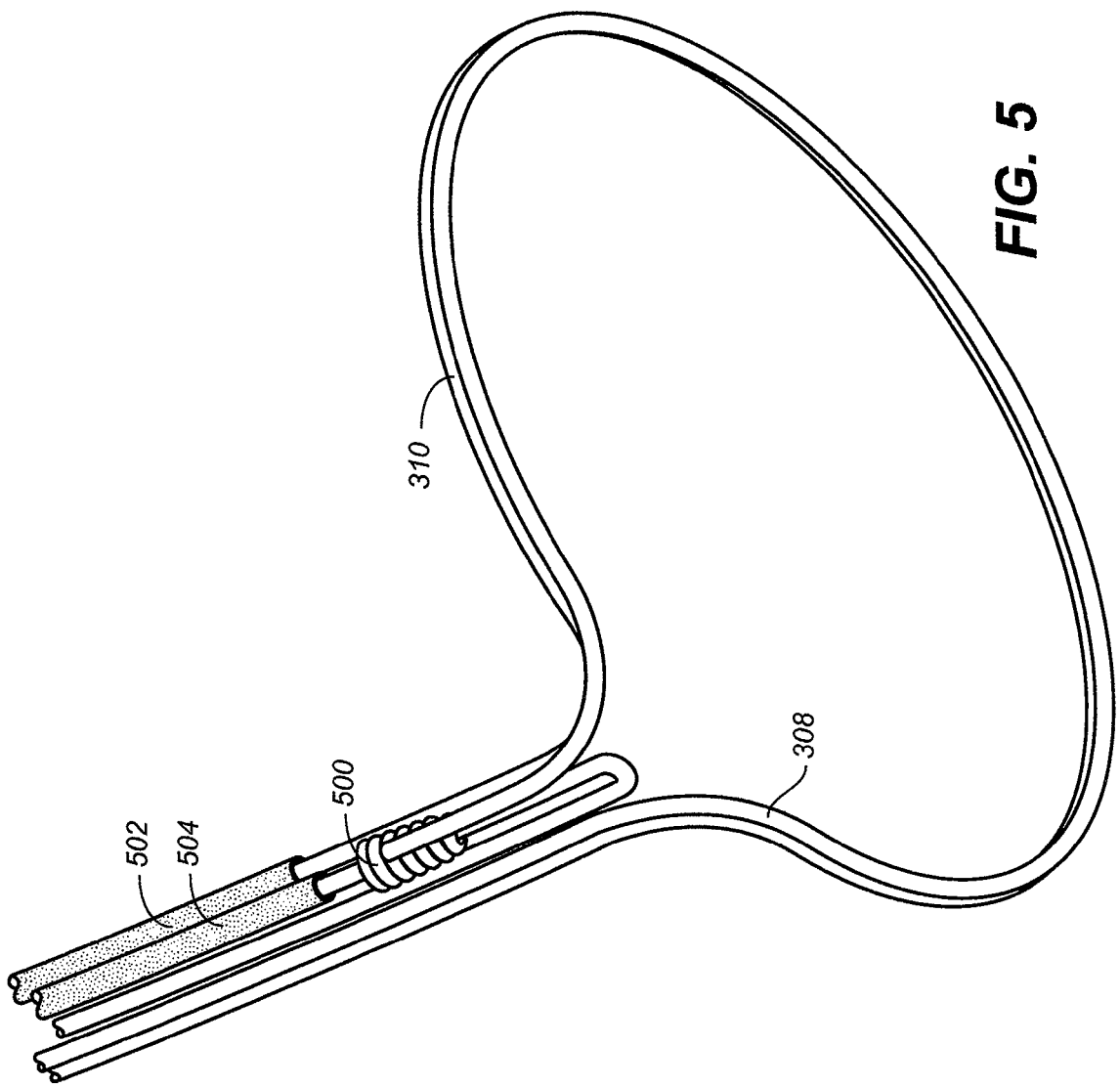

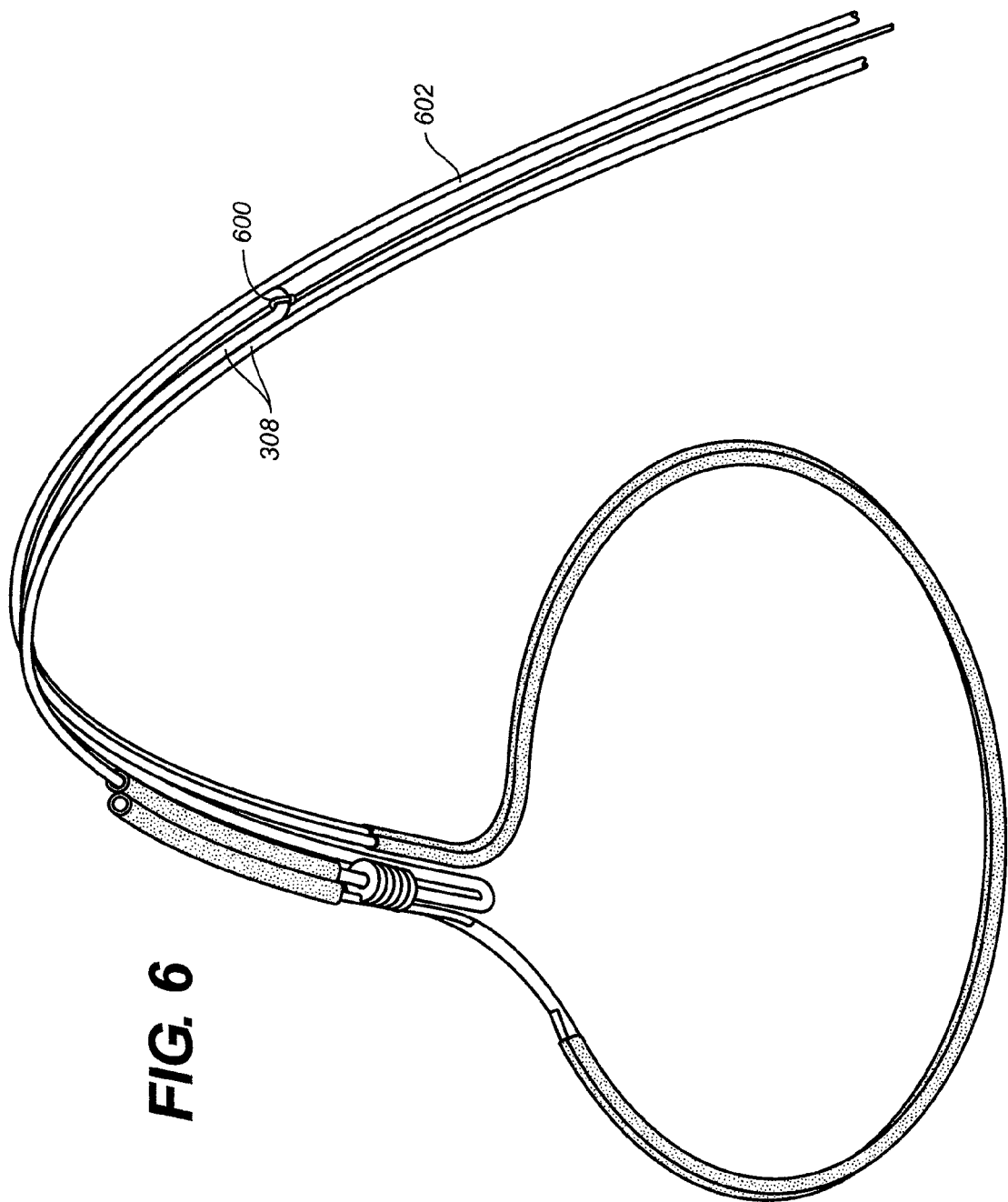

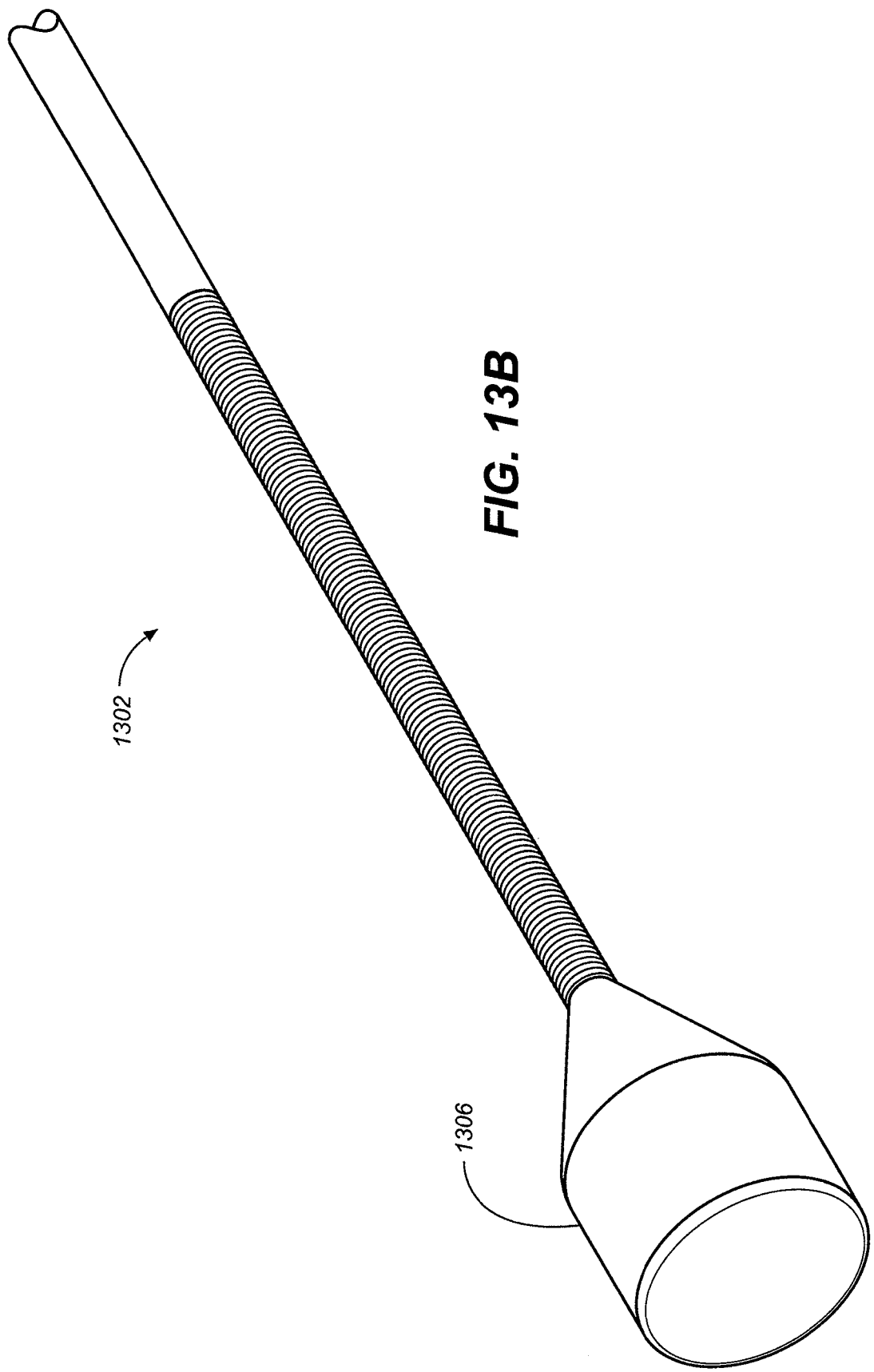

DEVICES, SYSTEMS, AND METHODS FOR CLOSING THE LEFT ATRIAL APPENDAGE

CROSS-REFERENCE TO RELATED APPLICATIONS

This application is a continuation of U.S. patent application Ser. No. 12/055,213, filed on Mar. 25, 2008, now U.S. Pat. No. 8,771,297, which claims priority to U.S. Provisional Patent Application Ser. No. 60/921,002, filed on Mar. 30, 2007, all of which are incorporated herein by reference in their entirety.

FIELD

In general, the devices, systems, and methods described here are for closing off a portion of tissue, e.g., the left atrial appendage, using a surgical, minimally invasive, or intravascular approach.

BACKGROUND

Atrial fibrillation is a common problem that afflicts millions of patients. Unfortunately, atrial fibrillation often results in the formation of a thrombus, or clot, in the appendage of the left atrium. This presents a problem, inasmuch as the thrombus can dislodge and embolize to distant organs, resulting in adverse events such as a stroke. For this reason, most patients with atrial fibrillation are treated with a blood thinner to help prevent the formation of a thrombus. Blood thinners, however, can present health risks (e.g., bleeding), particularly in the elderly, and often also require that the user make significant lifestyle changes.

Several methods have been developed to address the potential problem of thrombus formation in the left atrial appendage. One such method is suturing along the base, or ostial neck of the appendage, where it joins the atrial chamber. In this way, blood flow into the atrial appendage is cut-off, eliminating the risk of thrombus formation therein. This is typically done through open-heart surgery, making the availability of the procedure available to only those who are otherwise undergoing an open-heart procedure, or who are at particularly high risk. In addition, open-heart surgery requires general anesthesia and has a number of well-know risks, making it less desirable.

Other methods have also been investigated. For example, methods of stapling the base of the appendage and methods have been investigated, as have methods of filling the appendage with a space occupying, or occluding member. However, stapling is not a preferred method given the fragility of the appendage and the likelihood of its rupture. Occlusion devices may not effectively prevent all blood flow into the appendage, leaving areas of potential thrombus formation.

Additional devices and methods for closing the left atrial appendage would therefore be desirable. In particular, devices and methods for closing the left atrial appendage using minimally invasive, intravascular, or a combination of these techniques, would be desirable in order to avoid the need for opening the chest. Of course, additional devices for use in open surgical procedures are desirable as well, especially when those devices offer additional advantages over standard devices.

BRIEF SUMMARY

Described here are devices, systems and methods for closing the left atrial appendage. Some of the methods described here utilize one or more guide members having alignment members to aid in positioning of a closure device. In general, these methods comprise advancing a first guide having a first alignment member into the left atrial appendage, advancing a second guide, having a second alignment member, into the pericardial space, aligning the first and second alignment members, advancing a left atrial appendage closure device into the pericardial space and adjacent to the left atrial appendage, and closing the left atrial appendage with the closure device. In these variations, the closure device typically comprises an elongate body having a proximal end and a distal end, and a closure element at least partially housed within the elongate body. The closure element comprises a loop defining a continuous aperture therethrough.

Any of the devices used in any of the methods described here may be advanced under any of a variety of visualization techniques, e.g., fluoroscopic visualization, ultrasound, etc. For example, the first guide, second guide, or both guides may be advanced under fluoroscopic visualization in some variations. Similarly, any of the devices used in any of the methods described here may be advanced over a guide element or guide wire. For example, the first guide, second guide, closure device, any additional guide, or any combination thereof, may be advanced over a guidewire. In some variations, the second guide is coupled to the closure device for at least a portion of the method.

The alignment members may be, or may comprise, any suitable alignment member. For example, they may be or may comprise magnets, radiopaque markers, echogenic markings, members configured to produce one or more audible signals, interconnecting or interlocking members, one or more vacuum members, or the like. In some variations, the alignment members are magnets.

The first guide may further comprise an expandable member, e.g., an expandable cage, an expandable strutted structure, an expandable balloon, or the like. In some variations, the expandable member comprises an expandable balloon. The expandable member may be used for any suitable purpose, e.g., to atraumatically displace tissue, to help with identifying, sizing, protecting, isolating, stabilizing, or positioning tissue, or the like. In some variations, the expandable member is expanded within the left atrial appendage. In other variations of the methods described here, a third guide is advanced into the left atrial appendage, where the third guide has a proximal end and a distal end and comprises an expandable member. In some additional variations, the first and third guides are coupled together for at least a portion of the method. Again, the expandable member may comprise any suitable expandable member. In some variations, the expandable member is a balloon, which may or may not have one or more apertures therein. The apertures, for example, may be useful in enabling inflation and deflation of the balloon, may be useful for enabling passage of one or more guides or guidewires therethrough, or may be useful in enabling delivery of fluids, such as saline, contrast, drugs, etc., distal of the balloon.

The closure device may further comprise a suture for encircling the left atrial appendage after it has been closed with the closure device. Of course, the closure device may also have the ability to encircle the left atrial appendage without having a suture coupled thereto. The closure element alone may capture and release the left atrial appendage (i.e., it can open and close around the left atrial appendage), which may help facilitate optimal closure of the left atrial appendage, prior to permanent exclusion. In some variations, where a suture is used, the suture may comprise a surgical slip knot. The suture may or may not be coupled to the closure element.

The methods described here may further comprise tensioning the suture. The methods may additionally comprise releasing the tension on the suture, e.g., to help facilitate repositioning of the device, and the like. The methods may further comprise releasing the suture from the closure element, tightening the suture, and severing the suture. When the methods include severing the suture, the suture may be severed in any suitable fashion. For example, the suture may be severed with a cutting element, or may be severed by the application of energy (e.g., light energy, thermal energy, RF energy, electrical energy, magnetic energy, electromagnetic energy, kinetic energy, chemical energy and combinations thereof). When a cutting element is used, it may be an element on the closure device itself, or it may be part of a separate device.

The methods described here may also include confirming satisfactory or optimal closure of the left atrial appendage prior to permanent exclusion, excluding or opening the left atrial appendage with the closure device, repositioning the closure device, reclosing the left atrial appendage, and permanently excluding the left atrial appendage.

Other methods for closing the left atrial appendage are also described. In these methods, a closure device is advanced into the pericardial space and adjacent to the left atrial appendage, the left atrial appendage is closed with the closure device, the left atrial appendage is secured with a suture, and then the suture is severed. In these variations, the closure device typically comprises an elongate body having a proximal end and a distal end, and a closure element that comprises a loop defining a continuous aperture therethrough.

As with the methods described just above, the severing of the suture may be accomplished in any suitable fashion. For example, the suture may be severed with a cutting element, or by the application of energy (e.g., light energy, thermal energy, RF energy, electrical energy, magnetic energy, electromagnetic energy, kinetic energy, chemical energy and combinations thereof). When a cutting element is used, it may be an element on the closure device itself, or may be part of a separate device, or some combination of both may be used.

The closure device may comprise one or more expandable elements, and the closure device, the suture, or both may comprise a radiopaque material, echogenic material, or some combination thereof. In some variations, the closure device is made from a shape-memory material (e.g., a nickel titanium alloy, or the like), and in some variations, the suture is coupled to the closure device. In these methods, the closure device may be visualized while advanced, e.g., using fluoroscopy, ultrasound, a combination thereof, etc., and may or may not be advanced over a guide element or guidewire.

Additional methods for closing a left atrial appendage are also described here. These methods typically comprise advancing a first guide having a proximal end and a distal end into the left atrial appendage, through the left atrial appendage, and out of the left atrial appendage, such that one of the proximal or distal ends is within the vasculature, and one of the proximal or distal ends is within a subthoracic space, and advancing a left atrial appendage closure device into the pericardial space and adjacent to the left atrial appendage, and closing the left atrial appendage with the closure device. In these methods, the closure device typically comprises an elongate body having a proximal end and a distal end, and a closure element housed within the elongate body, where the closure element comprises a loop defining a continuous aperture therethrough.

In these methods, the proximal end of the first guide may be within the vasculature, or within the subthoracic space. In some variations, the closure device is advanced into the pericardial space over the first guide. Again, as with all the methods described here, any of the devices may be advanced under any of a variety of visualization techniques. For example, the first guide, closure device, or both may be advanced under fluoroscopic or ultrasound visualization, or both. In some variations, the methods further comprise advancing a second guide into the left atrial appendage, where the second guide has a proximal end, a distal end, and comprises an expandable member. The expandable member may be any suitable expandable member (e.g., expandable struts, expandable cage, expandable balloon, or the like). In some variations, the first and second guides are coupled together for at least a portion of the method.

Devices for closing the left atrial appendage are also described here. Some of the devices described here comprise an elongate body having a proximal end and a distal end, a closure element comprising a loop defining a continuous aperture therethrough at least partially housed within the elongate body, and a suture loop. The suture loop may or may not be coupled to the closure element. For example, the device may further comprise a retention member, where the retention member is configured to retain the closure element and the suture loop. The retention member may be configured to accomplish this task in any suitable fashion. For example, it may comprise first and second lumens, where the closure element is housed within the first lumen and the suture loop is housed within the second lumen. The second lumen may have a weakened region, a perforated region, or a slit or other opening configured to release and/or close the suture with the application of a force. In other variations, the retention member and the closure element are withdrawn or otherwise removed, leaving behind and/or closing the suture loop. In still other variations, the retention member comprises a first lumen and one or more releasable retention elements, where the closure element is housed within the first lumen and the suture loop is retained by the one or more releasable retention elements. The retention element may be any suitable element, for example, a releasable prong, a polymer tack, and the like.

The closure element may be made from any suitable material. In some variations, the closure element is made from a shape-memory material (e.g., a nickel titanium alloy). Similarly, the suture loop may be made from any suitable material (e.g., any suitable material useful for exclusion or closure). It may be bioabsorbable (e.g., biodegradable polymers, etc.), or non-bioabsorbable (e.g., non-biodegradable polymers, metals, etc.). The closure element, suture loop, or both may comprise a radiopaque or echogenic material.

In some variations, the elongate body has one or more curves along its length. The elongate body may or may not be steerable, and may or may not be configured as a catheter. In some variations, the closure element and the suture loop are separately actuatable. In other variations, the device further comprises a cutting element.

Systems for closing a left atrial appendage are also described here. Typically, the systems comprise a first guide having a size and length adapted for accessing the left atrial appendage through the vasculature, where the first guide comprises a first alignment member, a second guide having a size and length adapted for accessing the pericardial space from a subthoracic region, where the second guide comprises a second alignment member, and a closure device comprising an elongate body having a proximal end and a distal end, and a closure element housed at least partially therein, where the closure element comprises a loop defining a continuous aperture therethrough. The system may further comprise any suitable or useful device or component.

For example, in some variations the system further comprises an expandable member. The expandable member may be any suitable expandable member, and in some variations the expandable member is an expandable balloon with or without one or more apertures therein. The expandable member may be configured to be couplable to the first guide.

The systems described here may further comprise a suture, which may or may not be coupled to, or couplable with, the closure device. The systems may also comprise a device or element for severing the suture. In some variations, the closure device is couplable to the second guide.

The first and second alignment members may be any suitable alignment members. For example, they may be or may comprise magnets, radiopaque markers, echogenic markings, members configured to produce one or more audible signals, interconnecting or interlocking members, one or more vacuum members, or the like. In some variations, the alignment members are magnets, which may or may not be located at the distal ends of the first and second guides. The systems may further comprise instructions for using the first guide, second guide, closure device, or any combination thereof. In some variations, the elongate body of the closure device has one or more curves along its length, and the systems further comprise a straightening tube, configured to temporarily straighten the one or more curves.

BRIEF DESCRIPTION OF THE DRAWINGS

FIGS. 2A-2B are different views of an illustrative device that may be used with the systems and methods described herein.

FIG. 3A provides a close-up view of a distal end of an illustrative device having a retention member.

FIG. 4 provides a close-up view of a distal end of an illustrative device, without a retention member.

FIG. 5 is a depiction of an illustrative device with the catheter body removed for purposes of description and clarity.

FIG. 6 provides another depiction of an illustrative device with the catheter body removed, here, showing more of the device.

FIGS. 13A and 13B are illustrative guides having alignment members.

DETAILED DESCRIPTION

Figure 1:
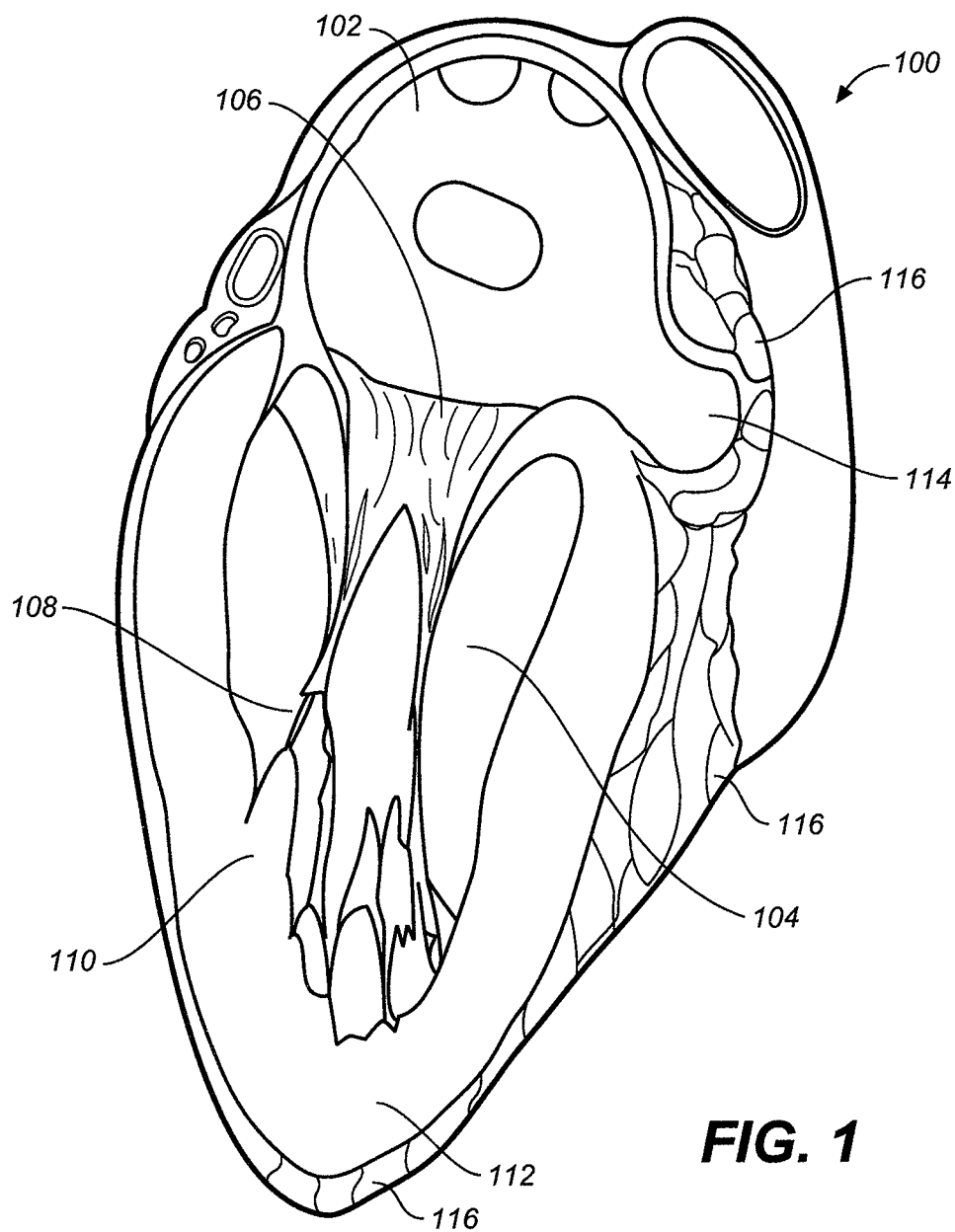
FIG. 1 provides a cross-sectional representation of a heart showing various anatomical structures.

Described here are devices, systems, and methods for closing the left atrial appendage. In this regard, it may be helpful to start by briefly identifying and describing the relevant heart anatomy. Shown in FIG. 1 is a cross-sectional view of the heart (100). Shown there is left atrium (102) and left ventricle (104). In between the left atrium (102) and the left ventricle (104) is the mitral valve (also known as the bicuspid valve), which is defined by a pair of mitral valve leaflets (106). The leaflets are connected to chordae tendinae (108) that are in turn, connected to papillary muscles (110). The papillary muscles join ventricular wall (112). The left atrial appendage (114) is shown adjacent to, and is formed from, the wall of the left atrium (102).

As can be seen, the left atrial appendage (114) lies within the boundaries of the pericardium (116), and is in close proximity to the ventricular wall (112). The left atrial appendage typically has a tubular shape that approximates a cone, with a slight narrowing or neck in the plane of the orifice where it joins the left atrium (102). In patients with atrial fibrillation, the left atrial appendage (114) is the most common location for thrombosis formation, which, in time, may dislodge and cause a devastating stroke. Because stroke is the primary complication of atrial fibrillation, the left atrial appendage is frequently excluded from the left atrium in those patients undergoing procedures to treat atrial fibrillation, and is often removed or excluded at the time of other surgical procedures, such as mitral valve surgery, to reduce the risk of a future stroke. The devices and systems described here, help ensure proper closure of the left atrial appendage, at the neck or base of the left atrial appendage, along the anatomic ostial plane. In this way, exclusion of the entire left atrial appendage from systemic circulation may be facilitated.

I. Devices

The devices described here for closing the left atrial appendage generally comprise a closure element having one or more loops. The devices may be suitable for use with minimally invasive access to the left atrial appendage (e.g., through a small sub-xyphoid or other intercostal incision, through an incision in the costal cartilage, through a port, through the vasculature, etc.) or may be suitable for use with open surgical procedures. The lengths of the devices may be chosen as desirable.

Figure 2B:
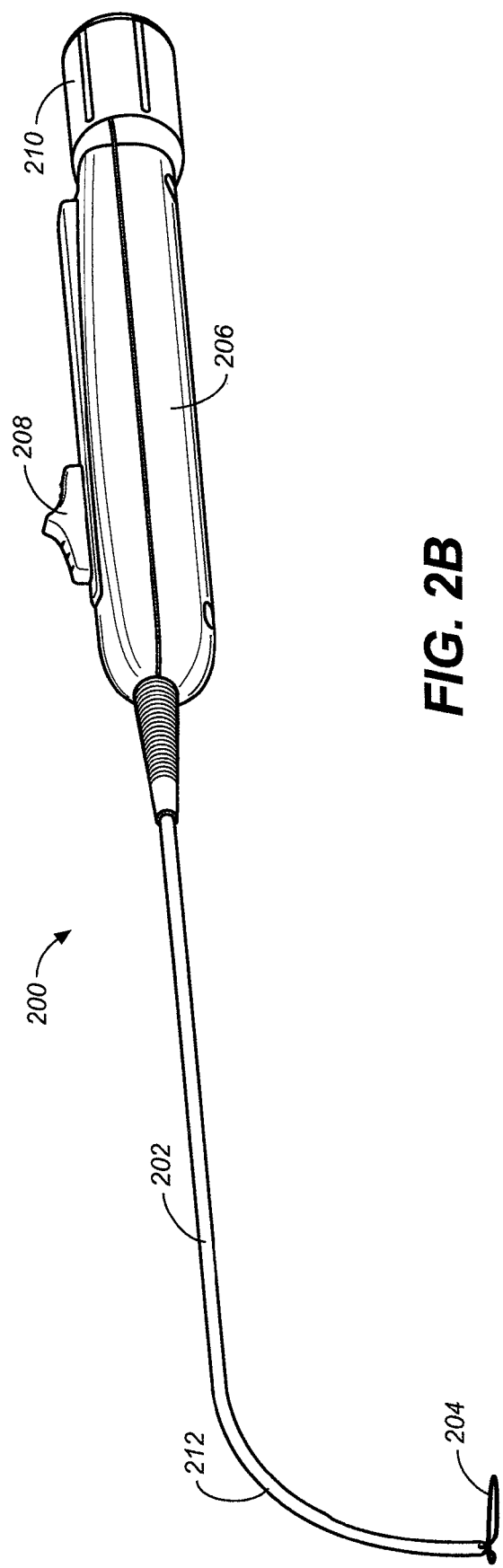

FIGS. 2A and 2B provide different views of an exemplary device that may be used to close the left atrial appendage. Shown in FIG. 2A is device (200) comprising an elongate body (202) having a proximal end and a distal end, and a closure element (204). In this variation, the closure element comprises a loop that defines a continuous aperture therethrough suitable for encircle the left atrial appendage therein. The closure element is at least partially housed within the elongate body (202) and may be advanced therefrom, or retracted therein. Also shown in FIG. 2A is a lumen (214) for passage of a tools or fluids therethrough. For example, the lumen (214) may enable passage of a guide (with or without an alignment member), a guidewire, a suture cutter, fluids and/or drugs, and the like. Any number of lumens may be used for any suitable purpose. Suitable lumens will be described again with reference to FIG. 8. Also shown in FIGS. 2A and 2B is handle (206) having a linear actuation slide (208) and knob (210). Additional details of the handle will be discussed below.

In the variation shown in FIGS. 2A and 2B, the elongate body (202) comprises a curve (212) at a distal portion thereof. In instances where the elongate body (202) of the device comprises one or more curves, a straightening tube, or other straightening mandrel or mechanism may be used to temporarily straighten the elongate body during delivery (e.g., until the pericardial space is reached). After a particular location has been reached, the straightening tube or mandrel may then be withdrawn. The straightening tube may be made of any suitable material (e.g., a rigid plastic, stainless, combination thereof, etc.). Of course, it should be understood that the device need not comprise one or more curves as shown in FIGS. 2A and 2B. For example, the elongate body may be straight and flexible, and a pre-curved tube or mandrel may be employed during the methods to aid in delivery and use (e.g., while advanced to the left atrial appendage). Similarly, the elongate body may be straight and flexible, and have a pull wire attached thereto, so that when the pullwire is pulled proximally, the elongate body flexes and bends. In this variation, the elongate body may be maneuvered as appropriate. It should be understood that any of the devices described here may be configured for steerability, or may be configured for robotic use (e.g., configured for use with one or more robotic or other automated type device).

FIG. 3A provides additional detail of a suitable closure element. Shown there is a distal portion (300) of a suitable closure device having an elongate body (302) and a closure element assembly (304). In FIG. 3A, details of an elongate body extension, or tip (306) can be seen. This tip may be thermoformed or injection molded, or may be integral with the rest of the elongate body (302). In instances where a suture loop (308) is used, the tip (306) may serve to house a suture knot therein. It should be understood that when reference is made to the elongate body, it is meant to include any such tip (306) as shown in FIG. 3A. Also apparent in FIG. 3A is suture loop (308), which is shown passing through the tip (306) in a proximal direction and into a retention member (312) in a distal direction. Also shown passing through tip (306) in a proximal direction and into retention member (312) in a distal direction is closure element (310), which will form a loop to encircle the left atrial appendage. As can be seen by FIG. 3A, the retention member is configured to retain the closure element and the suture loop.

Figure 3B:
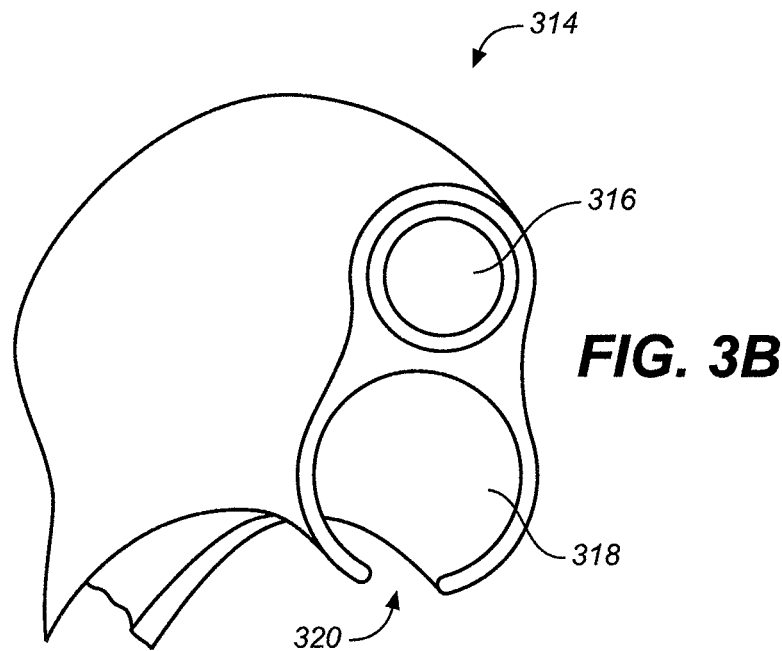
FIGS. 3B-3D depict illustrative retention members that may be used with the devices described herein.
Figure 3C:
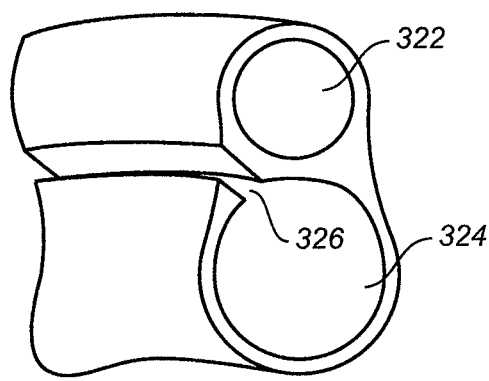
Figure 3D:
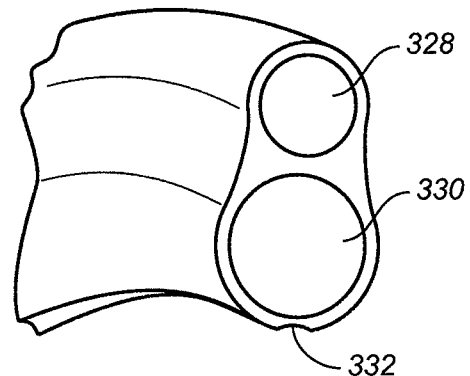

FIGS. 3B-3D depict illustrative retention members that may be used with the devices described herein. FIG. 3B shows an end view of a retention member (314) having first and second lumens (316, 318) for retaining a closure element and a suture loop therein. In this variation, the second lumen (318) has a slit or other opening (320) along its length, for allowing the suture to pass therethrough when it is ready to be deployed. Of course, it should be understood that the first and second lumens may be positioned or oriented in any suitable way with respect to each other, and similarly, the slit or other opening on the second lumen may be positioned or oriented in any suitable fashion with respect to the first lumen (e.g., it may be approximately 180°, approximately 150°, approximately 120°, approximately 90°, approximately 60°, approximately 30°, or the like, from the first lumen (316)). FIG. 3C provides an illustration of a retention member having a first lumen (322), a second lumen (324), and a slit (326). In this variation, the slit (326) is positioned closer to the first lumen (322) than the slit of FIG. 3B. The width or spacing of the slit opening may selected as desired or appropriate. Similarly, the slit need not extend or be continuous along the entire length of the retention member. In some variations, the slits may have prongs or arms along its length to help capture and retain the suture therein. In other variations, the slits may be covered at spaced apart locations therealong with a biodegradable polymer, temporarily used to tack or hold down the suture. Of course, in still other variations, the retention member does not comprise a slit, and instead comprises some other type of retention mechanism, such as the prongs or tacks described just above. In yet other variations, there are no slits or openings in the retention member and the suture loop is released upon removing or withdrawing the retention member and closing the device.

FIG. 3D provides another variation of a retention member. In this variation, the retention member has a first lumen (328), second lumen (330), and a separation region (332). The separation region may be constructed in any suitable fashion. For example, the separation region may comprise a perforated region adapted to perforate and release the suture with the application of force. Alternatively, the separation region may be a thin-walled or other type of weakened region that may be configured to break and release the suture. It should be understood that the retention member may have any suitable geometry or shape, and may be made from any suitable material. Similarly, the lumens need not be full circles or have a circular cross-sectional geometry. When these or other types of retention members are used, the suture loop may be torn out, pulled through, or otherwise released from the retention member after it has been properly positioned and tightened as desirable.

The above described components may be made of any suitable material. For example, the closure element may be made from a shape-memory material, such as a shape-memory alloy (e.g., nickel titanium alloy, etc.), may be made from stainless steel, polyester, nylon, polyethylene, polypropylene, some combination thereof, etc. Similarly, the suture loop may be made of any suitable material useful in exclusion or closure, and the term "suture loop" should be understood accordingly. For example, it may be made of a biodegradable material (e.g., polylactic acid, polyglycolic acid, polylactic-co-glycolic acid, etc.), or may be made of a non-biodegradable material (e.g., metal, steel, polyester, nylon, propylene, silk, and combinations thereof). In some variations, as will be described in more detail below with reference to the methods, the suture loop is made from a biodegradable material such that the suture loop degrades after a period of time has elapsed (e.g., for sufficient scarring to be achieved). It should be understood, the any part of the device may comprise, include, or be made from a radiopaque or echogenic material to help facilitate visualization. For example, the closure element, the suture loop, the elongate body, or any combination of these components may comprise a radiopaque or echogenic material.

The suture loop and the closure element may be configured to have any appropriate perimeter. For example, they may have a perimeter of 4.5 inches in a fully expanded state, a perimeter of about 4.3 inches, about, 3.3 inches, about 4.0 inches, about 3.5 inches, about 3.3 inches, 3.0 inches, about 2.7 inches, about 2.5 inches, about 1.5 inches, about 1.25 inches, or the like. Of course, these perimeters will vary as the closure element and suture loop are actuated and retracted.

For additional clarity, FIG. 4 provides a view of distal portion (300) of FIG. 3A, without retention member (312), thus showing the looped nature of closure element (310) and suture (308). FIG. 5 is a view of distal portion (300), without retention member (312), tip (306), and elongate body (302), thus providing additional details of this variation of the device. Shown there is of course, closure element (310) and suture (308). Suture (308) further comprises a surgical knot (e.g., a one way slipknot or other suitable knot) (500). Also shown is an anchoring feature (502), here shown as a tube, for anchoring one side of the closure element (310). The opposite side of the closure element is the active or actuation side (i.e., one side remains anchored while the other side has additional active length). Of course, when anchoring is used, it may be done in any suitable way. In other variations (not shown here), both sides of the closure element are active and actuatable (i.e., neither side is anchored). The device may also comprise a suture tube (504) for facilitating suture passage.

Figure 7:
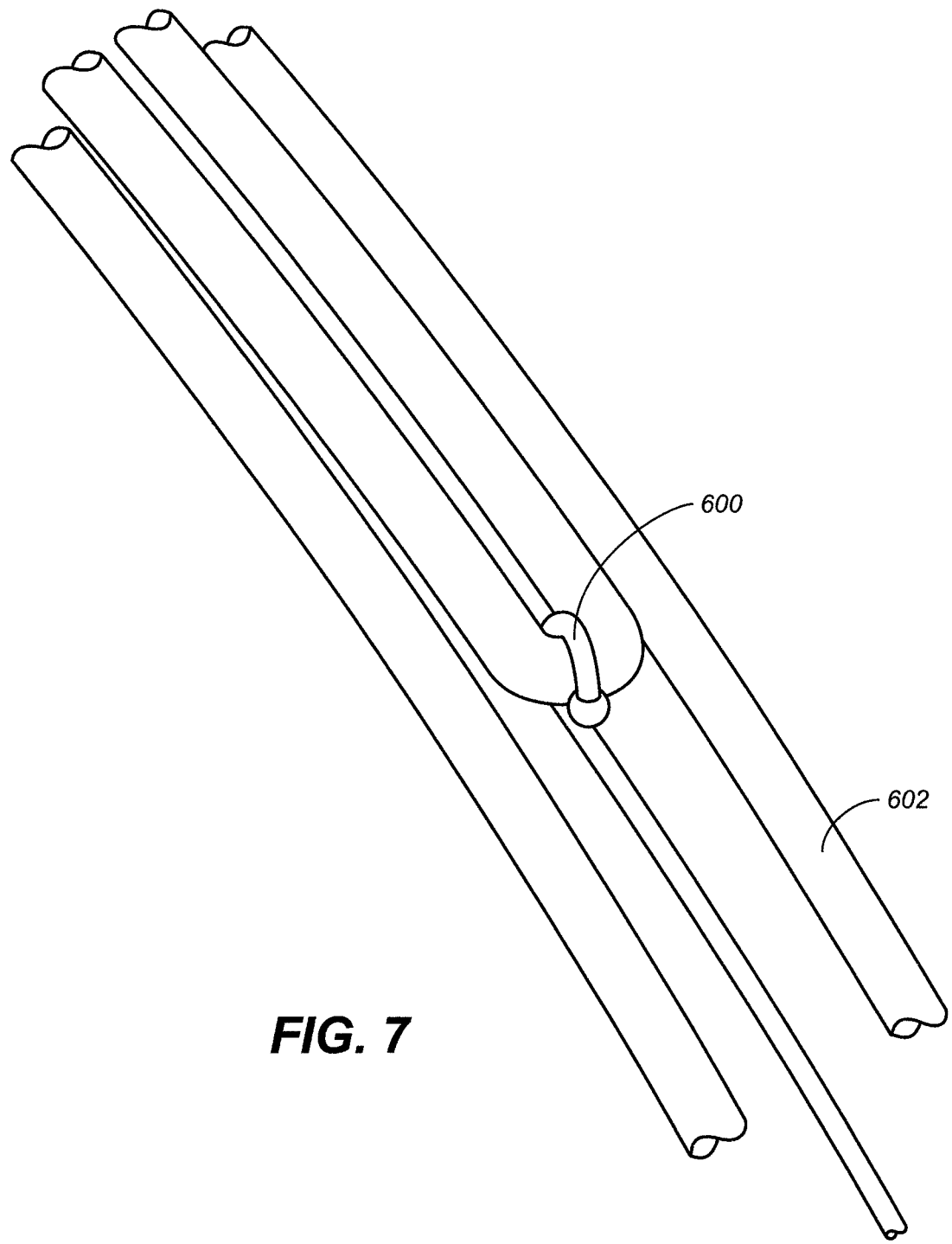
FIG. 7 is a close-up view of an illustrative suture retention mechanism, here, shown as a suture hook.

FIG. 6 shows additional proximal detail of a suitable closure device. In this view, the elongate body and tip have been removed, but the retention member remains. Of particular interest here is suture hook (600). Suture hook (600) captures suture loop (308) so that the closure element (310) may be advanced and retracted separately from suture loop (308) when the two are coupled together. That is, the suture hook (600) prevents the suture from tightening as the closure element is actuated, so that the device may be positioned as desirable before the suture is actuated. The suture hook (600) may also help prevent excess suture from opening and closing, and thus help prevent excess suture from getting caught on anatomical structures, instruments, etc. Also shown in FIG. 6 is a proximal length of the closure element (602). In some variations, it may be useful to have at least a portion of the proximal length of the closure element (602) coated with a lubricious coating, in order to help facilitate slidable actuation. Any suitable lubricious coating may be used (e.g., PTFE, etc.). The suture hook (600) is shown in greater detail in FIG. 7. While the suture hook shown in FIG. 7 has a rounded atraumatic tip, it need not be so. Indeed, any suitable tip may be used. The suture hook may be made of any suitable material.

Figure 8:
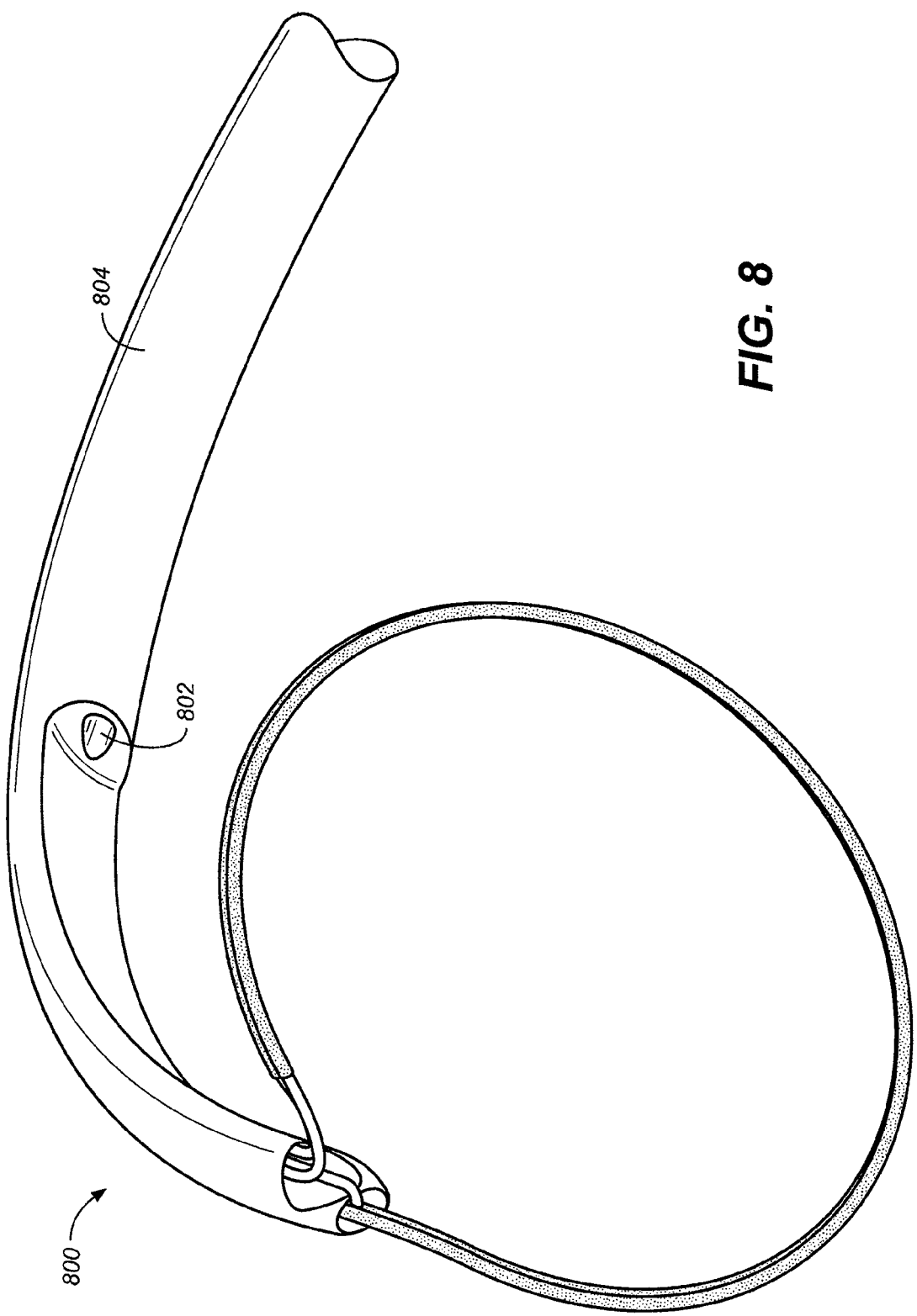
FIG. 8 is a close-up view of a distal end of an illustrative device having a lumen therethrough.

FIG. 8 provides details of the distal portion of an illustrative closure device (800), here comprising at least one lumen (802) in the elongate body (804). The lumen may be used for any suitable purpose. For example, it may be used to enable passage of one or more guides or guidewires therethrough, one or more tools therethorugh, or the like. The lumen may also be used as a flush lumen, a vacuum lumen, a drug delivery lumen, or the like. The elongate body may comprise any number of lumens, and it should be understood that the lumens need not traverse the entire length of the elongate body, nor form a completely bounded aperture (i.e., the use of lumens herein is intended to capture instances where a slit or groove may be used with one or more guides, guidewires, or additional tools).

Figure 9:
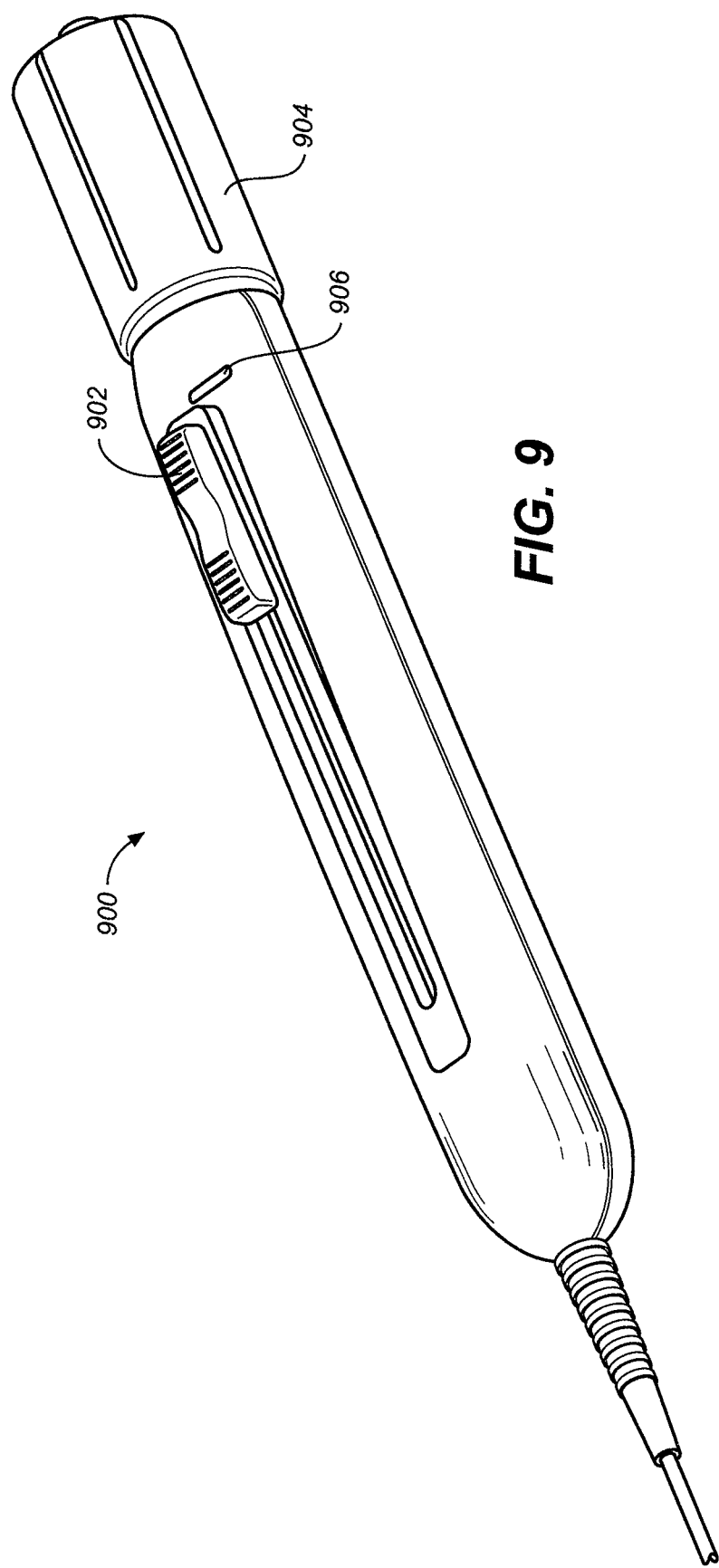
FIG. 9 is a top side view of one variation of the proximal end of the devices described here.

FIG. 9 is one variation of a suitable handle (900) for the devices described herein. In this variation, the handle comprises a linear actuation slide (902) for actuating the closure element, and a suture knob (904) for actuating the suture. While not shown, the suture hook, described above, or similar such feature, helps enable the separate actuation capability described here. Thus when the slide (902) is pushed distally, the closure element, which has been at least partially retained within the elongate body, will be advanced distally, and the loop size of the closure element will get bigger. Conversely, when the slide is retracted proximally, the closure element will be retracted and the loop size will get smaller. The suture loop is not affected in this process. Instead, the suture loop in this variation is controlled by the suture knob. Of course, the suture loop need not be actuated by a knob. That is, the suture may be separately actuated by an additional slide, lever, button, or the like. Similarly, the closure element need not be actuated by a slide. It may be actuated by a button, knob, lever, or the like.

Figure 10:
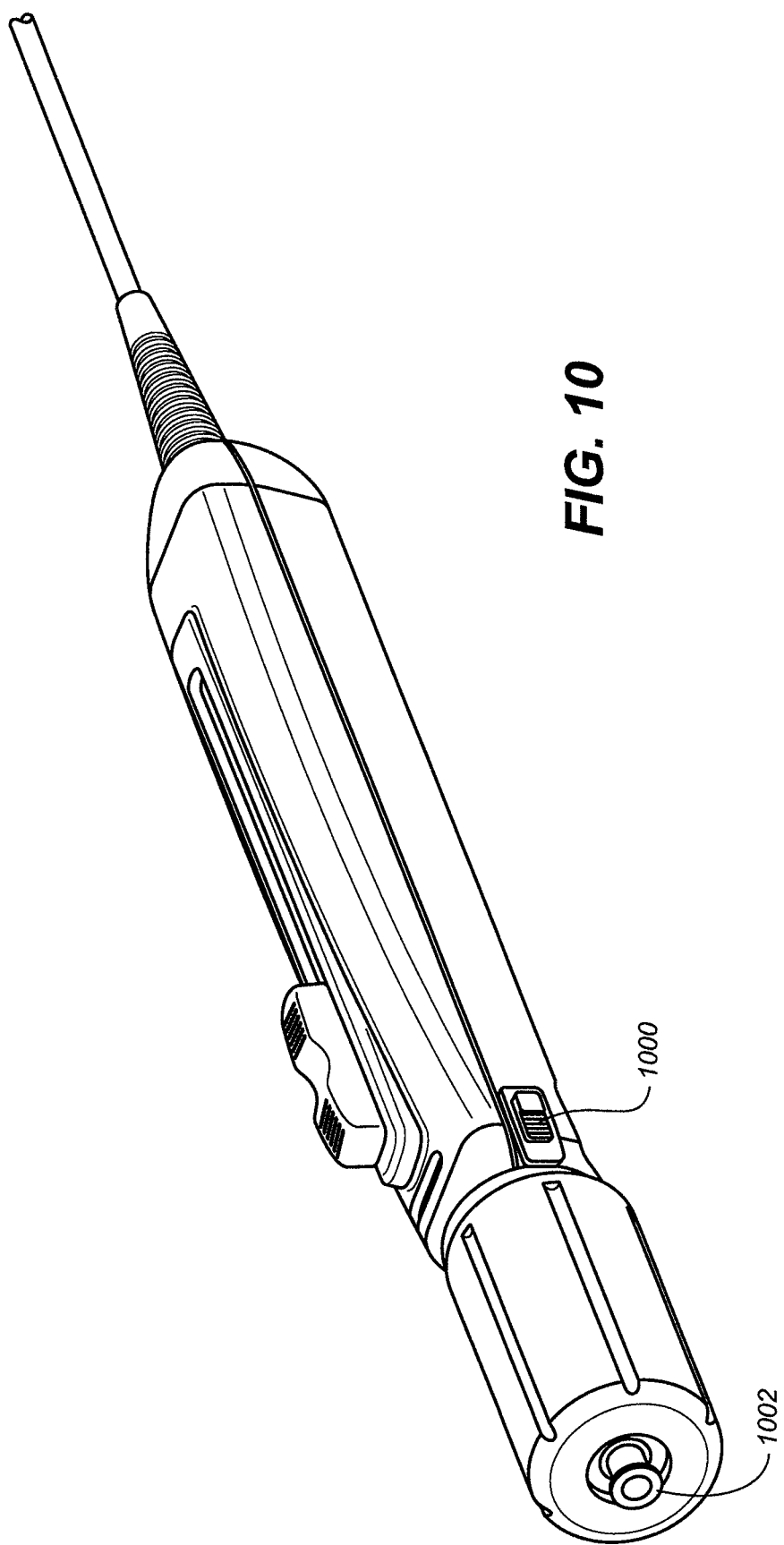
FIG. 10 is a skewed end view of one variation of the proximal end of the devices described here.

Also shown in FIG. 9 is suture cutting slot (906). While not easily shown in this view, the suture runs through the handle and into the knob. The suture cutting slot enables the suture to be cut easily, as the suture traverse the slot and the slot provides a viewing window and access point for suture severing. Of course, the suture need not be severed in such a fashion. In some variations, the closure device itself comprises a cutting element for severing the suture (e.g., a blade actuated by a button or some other mechanism). FIG. 10 provides a skewed end view of the handle shown in FIG. 9 so that additional details may be seen. Specifically, shown here are suture knob lock (1000) and luer fitting (1002) at the proximal end of the handle lumen.

Figure 11:
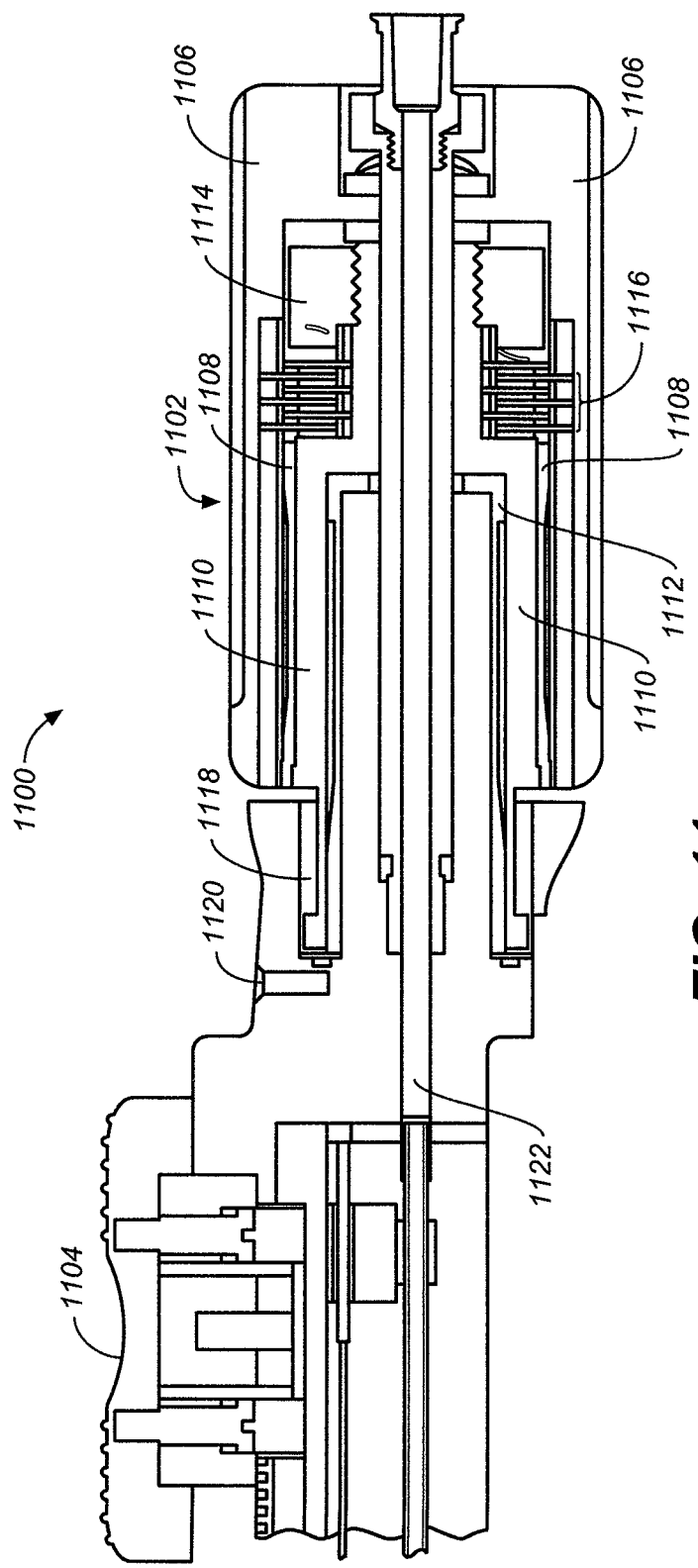
FIG. 11 provides a cross-sectional view of one variation of the proximal end of the devices described here.

FIG. 11 provides a cross-sectional view of a portion of handle (1100), here showing a length of the handle including the suture knob (1102) and the slide actuator (1104) in its most retracted position. Suture knob (1102) comprises an outer knob (1106), and outer knob bearing (1108), inner knob (1110) and inner knob bearing (1112), thrust bearing (1114) and slip clutch plates (1116) that when actuated (when the knob (1102) is turned or rotated) apply a tension upon the suture loop causing it to release from the retention member. In one variation, the slip clutch plates (1116) have particular force settings and are configured to provide tactile feedback to the operator indicating closure. In other variations, the clutch plates (1116) may have a particular force limitation in order to protect against shearing or cutting of tissue by the suture during release or tightening of the suture loop. For example, in these variations, once the suture loop reaches a pre-determined force, the outer knob (1106) and outer knob bearing (1108) may disengage from inner knob (1110) and inner knob bearing (1112) by slipping or the like (e.g., similar to a gas cap when overtightened).

Also shown is a suture reel area (1118) and a suture severing slot (1120), which, as described briefly above, is used to help terminate the suture by placement of blade, scalpel, or other sharp instrument therein. As described above, in some variations, the closure device itself comprises a suture cutting device or mechanism, and this may be located at the same place as the suture severing slot (1120) or some other place. For example, the device may include a blade or other cutting mechanism that may be actuated by a blade, lever, knob, etc., whether or not located in the suture severing slot location. Lumen (1122) may be used for placement of a guide (with or without an alignment member), guidewire, one or more tools (e.g., a suture cutter, visualization devices, etc.), one or more fluids (e.g., saline, drugs, etc.), as described above.

II. Methods

Methods for closing the left atrial appendage are also described here. The left atrial appendage may be accessed in any suitable fashion, and any of the devices described here may be used. For example, the left atrial appendage may be accessed from the inside of the heart, or may be accessed from the outside of the heart. In some variations, the left atrial appendage is accessed from both the inside of the heart, and the outside of the heart. Typically, the appendage is closed off from the outside of the heart, even when accessed from the inside of the heart.

In variations when the left atrial appendage is accessed from both the inside and the outside of the heart, it may be useful to employ the use of guides having alignment members. In this way, accessing the left atrial appendage may be more easily facilitated. It may also be useful to employ the use of a positioner or stabilizer, to help position devices relative to the left atrial appendage and to stabilize the appendage while it is being closed off. The positioner or stabilizer may be any suitable stabilizer or positioner, e.g., an expandable member or the like. More details of this will be described below.

In some variations, the methods of closing the left atrial appendage comprise advancing a closure device into the pericardial space and adjacent to the left atrial appendage, closing the left atrial appendage with the closure device, securing the closed left atrial appendage with a suture, and then severing the suture. The closure device may be any suitable closure device, such as a device having an elongate body with a closure element comprising a loop defining a continuous aperture therethrough, as described above. The suture may be severed in any suitable fashion, and at any suitable location along its length (i.e., from immediately adjacent to the knot at the left atrial appendage to just proximal to, or just distal to, the skin surface). In some instances it may be desirable to sever the suture at the knot itself (e.g., in instances where it is desirable to release tension on the suture entirely).

Figure 12:
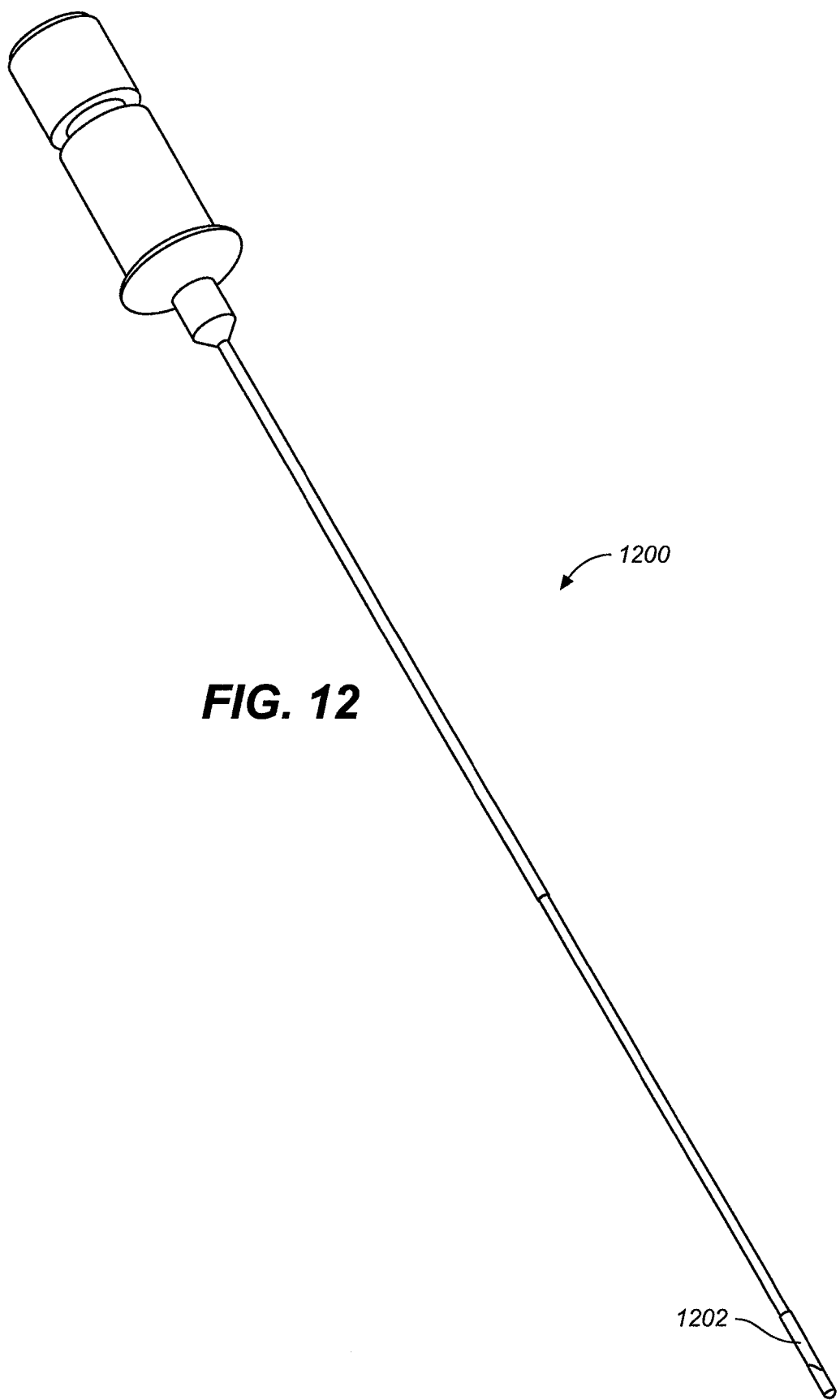
FIG. 12 is an illustrative suture cutter that may be used with the systems and methods described here.

An illustrative device (1200) for severing a suture is shown in FIG. 12. The device depicted there may be threaded over the suture and then actuated to cut the suture with a blade or similar cutting feature housed within distal portion (1202). While a device having a blade housed therein is depicted in FIG. 12, any suitable cutting device may be used, and the device may be made from or comprise any suitable materials (e.g., a radiopaque or echogenic material). In some variations, the closure device has a cutting element thereon, for cutting the suture. Of course, the suture need not be severed with a blade or other such cutting feature. The suture can be severed by the application of energy. For example, the suture may be severed with the application of light energy, thermal energy, RF energy, electrical energy, magnetic energy, electromagnetic energy, kinetic energy, chemical energy, and combinations of any of the above. Additional methods will now be described.

A. Transseptal and Pericardial Access

In some variations, the methods for closing the left atrial appendage include accessing the left atrial appendage from both the inside of the heart and the outside of the heart. In these variations, one or more guides having alignment members are often used to align the inside and outside access devices together. To access the inside of the heart, the vasculature is typically used. For example, access may be obtained via one or several of the various veins or arteries jugular, femoral, carotid, etc.). In some variations, the heart is accessed on the inside via the common femoral vein (e.g., the left common femoral vein) using a standard Seldinger technique with a needle. An introducer wire may then be advanced through the needle, followed by an introducer sheath. The introducer wire may then be removed. In some variations, a guiding catheter sheath may be placed as an alternative to an introducer sheath or the initial sheath may be replaced with a guiding catheter sheath.

Using fluoroscopy, an angiogram performed through the sheath, a catheter placed through the sheath, a guiding catheter sheath, or any combination thereof, may be performed to observe anatomical characteristics and considerations of the access route for the purpose of transseptal access into the left atrium (e.g., tortuosity, clots, devices, such as vena cava filters, etc.). Fluoroscopy, ultrasound, intracardiac echocardiography, extracardiac echocardiography, transesophageal echocardiography, or combinations thereof, may be used to help visualize transseptal access to the left atrium, and access to the left atrium may be obtained using standard transseptal access techniques.

For access to the heart from the outside, a subthoracic access point may be used. The access point is typically identified based on patient anatomic characteristics. In some variations, the access point is right of the xyphoid process and pointed towards the patient's left shoulder, but may be at any suitable location (e.g., intercostal access via a sternotomy, thoracostomy, or thoracotomy, or in the costal cartilage itself). Once the access point has been determined, a needle (e.g., a 17G Tuohy needle) may be advanced using standard pericardiocentsesis techniques under fluoroscopic guidance. After access to the pericardium has been obtained, a guidewire may be advanced through the needle under fluoroscopic visualization within the pericardiac sac. The needle may then be removed. Access to the pericardial space has thus been obtained.

Figure 13A:
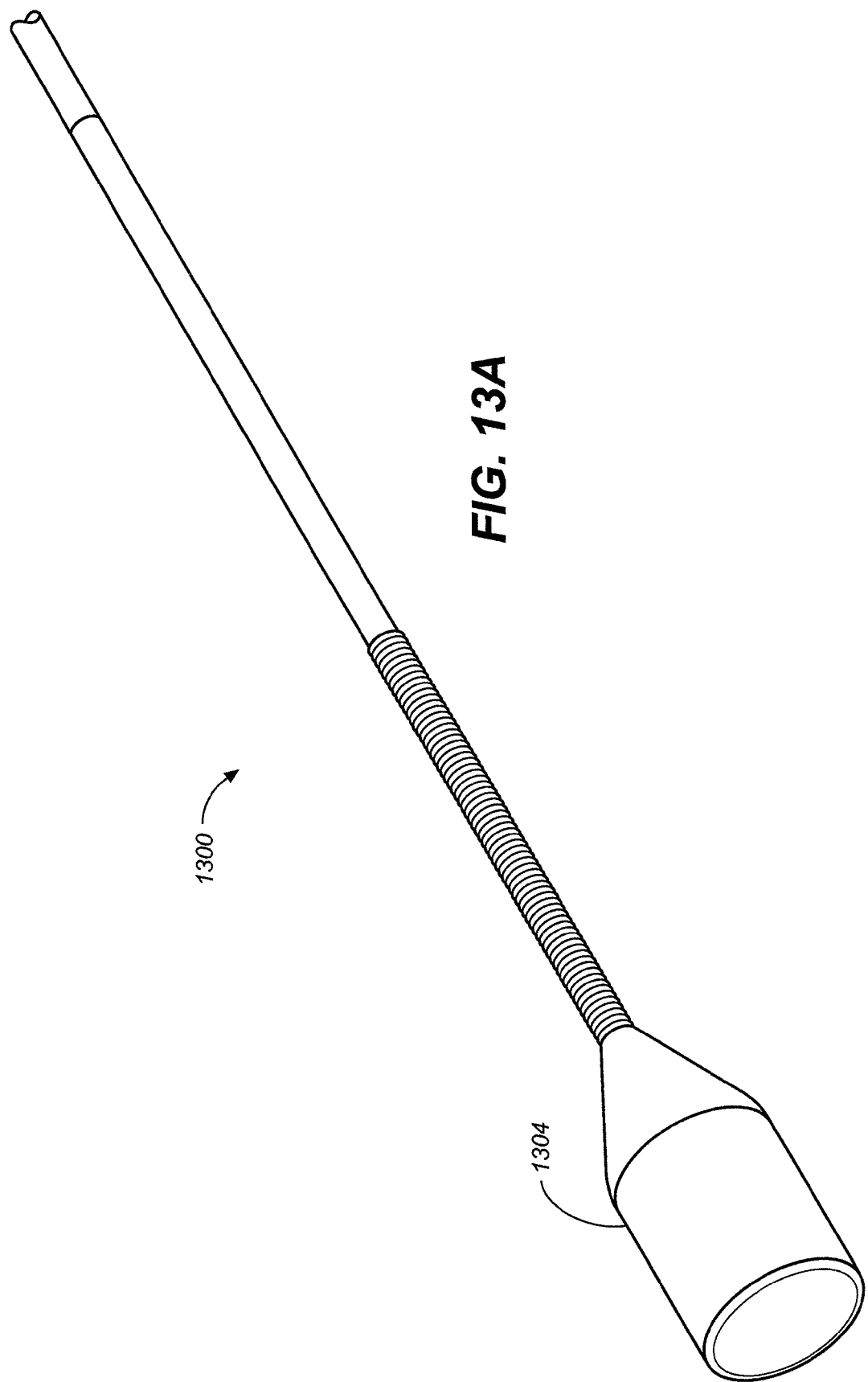

Turning now to the figures, after access from the inside and outside of the heart has been obtained using the above described devices and techniques, the devices of the current invention are ready for use. For example, first (1300) and second (1302) guides having alignment members as shown in FIGS. 13A and 13B respectively may be used to guide the procedure. The alignment member may be any suitable alignment member (e.g., interconnecting elements, one or more vacuum members, radiopaque or echogenic markers, members that are configured to produce an audible response, magnets, etc.). Here, the alignment members are magnets (1304, 1306) located at the distal ends of the guides. The magnets may be made from or comprise any suitable magnetic material, e.g., a rare earth magnet, such as neodymium-iron-boron, cobalt-samarium, or other powerful fixed magnet elements. These guides may be used for guiding additional tools and/or devices to the left atrial appendage.

The guides may have any suitable lengths and/or dimensions. For example, the guides may have a diameter of about 0.010" to about 0.050", about 0.020" to about 0.030", or the like. In some variations the first guide has a diameter of about 0.025" and the second guide has a diameter of about 0.035". Similarly, the length may be any suitable length. For example, from about 50 cm to about 300 cm or more, from about 100 cm to about 200 cm, from about 200 cm to about 250 cm, and the like. In some variations, the first guide has a length of about 250 cm and the second guide has a length of about 90 cm. The outer diameter of the alignment element may also be selected as desirable. For example, it may be from about 0.05" to about 0.2" or more. In some variations, the outer diameter of the alignment member of the first guide is about 0.106" and the outer diameter of the alignment member of the second guide is about 0.170". It should be understood that these dimensions are suitable for any guide, not only guides having alignment members comprising one or more magnets.

Figure 14A:
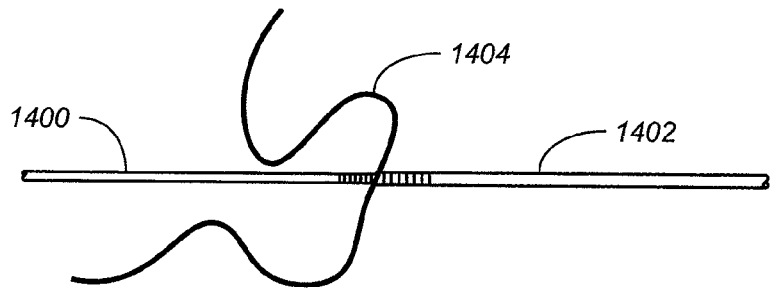
FIGS. 14A-14D depict an illustrative method of closing the left atrial appendage.
Figure 14B:
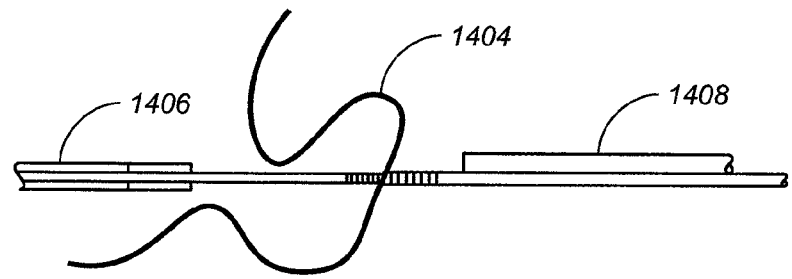

For example, turning to FIG. 14A, the first guide (1400) may be advanced into the left atrial appendage (1404), while the second guide (1402) may be advanced into the pericardial space adjacent to the left atrial appendage. Either of these guides may be advanced under any of a variety of visualization techniques, e.g., fluoroscopic visualization, ultrasound visualization, some combination thereof, etc. A balloon catheter (1406) or other expandable member may be advanced over the first guide, or in conjunction with the first guide (e.g., it may be coupled to or be part of the first guide) and into the left atrial appendage as shown in FIG. 14B. Similarly, a closure device (1408) may be advanced over the second guide, or in conjunction with the second guide (e.g., it may be coupled to or be part of the second guide), as shown in FIG. 14B.

In instances where a balloon is used as an expandable member, it may be made of any suitable material. For example, it may be made of polyisoprene, or other suitable materials. Similarly, the balloon may have any suitable dimensions. For example, it may have an outer diameter of approximately 10-40 mm, approximately 20-30 mm, or the like. Similarly, it may have any suitable length. For example, it may have a length of about 5 mm to about 50 mm, about 10 mm to about 20 mm, or the like. In some variations, the balloon has an outer diameter of approximately 20-30 mm, and a length of about 20 mm.

Figure 14C:
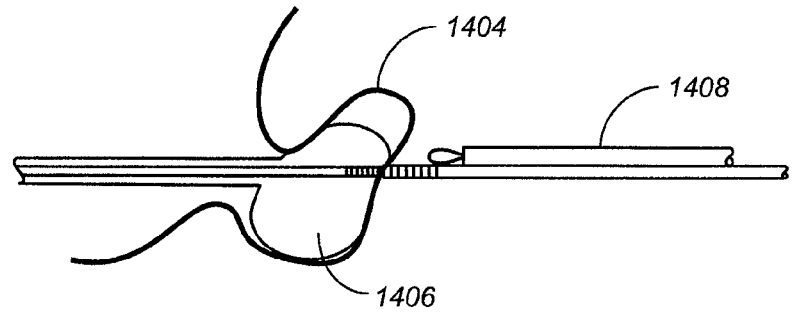

The expandable member (in this variation, shown as an expandable balloon) is inflated to position and stabilize the left atrial appendage, as shown in FIG. 14C. In its expanded state, the expandable member helps locate the ostial plane of the left atrial appendage. Specifically, when the expandable member is expanded, the left atrial appendage is distended and its shape is changed from roughly conical to roughly spherical, thus better defining the junction between the left atrial appendage and left atrium. In addition, the expandable member in its expanded state may be at a pressure much greater than that of the left atrium proper, resulting in a significant differential in tension between the left atrial appendage and the left atrium. The expandable member may have one or more apertures therethrough for passage of contrast to facilitate visualization.

Figure 14D:
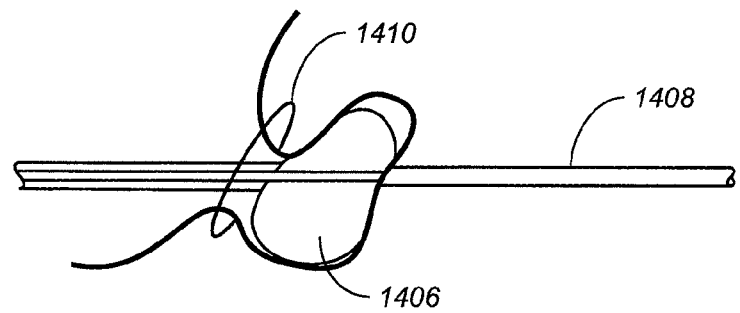

While the expandable member is still in its expanded state, a closure element (1410) of a closure device (1408) may be placed around the left atrial appendage and closed as shown in FIG. 14D. However, in some variations, the closure element is placed around the left atrial appendage while the balloon is in its deflated or unexpanded stated, and then the balloon is expanded. A suture may then be deployed from the device, tightened around the closed appendage, released from the device, and severed, leaving the closed appendage in place. Of course, in some instances it may be desirable to confirm proper closure of the appendage prior to tightening of the suture, and then again after the suture has been tightened using fluoroscopic or other visualization techniques. If closure is not adequate or otherwise not desirable, the loop may be opened, repositioned, closed, and then confirmed once again.

Specifically, it is desirable that the left atrial appendage be closed off as close to the anatomical ostial plane as possible (i.e., the opening that separates the left atrium from the left atrial appendage). If the left atrial appendage is closed off above the plane of the orifice (toward the left atrial appendage tip or away from the anatomical ostial plane), this may result in a persistent diverticulum of the left atrial appendage, which in turn may result in an additional site or nidus for thrombus formation despite complete exclusion of the left atrial appendage from the left atrium. In some individuals, the geometry of the left atrium and left atrial appendage may be such that the neck or narrowing between them is poorly defined from the epicardial, or outer aspect. In addition, the external geometry of the left atrial appendage-left atrial junction is difficult to differentiate from an epicardial perspective. This may be compounded by the fact that the anatomy is moving vigorously when the procedures are employed while the heart is beating and the lungs remain inflated (i.e., closed chest procedures). From an inside aspect, or endocardial view, fluoroscopy and ultrasound methods provide limited information or ability to landmark the true three-dimensional characteristics of the anatomic ostial plane. Thus the use of the devices described here help facilitate proper positioning and closure of the left atrium, and may be used during beating heart procedures, thus resulting in significant advantages over known left atrial appendage closure devices.

Of course, many variations on this method are possible. For example, the guides may be used as guidewires or rails for additional devices to slide over, or the guides may be coupled to the devices described just above. Additional guides or guidewires may also be used, and confirmation steps may be used throughout as appropriate. The guides having the alignment members thereon may be used or removed during the methods as appropriate or desirable. In some variations, the closure device has one or more bends or curves along its length, and a tip straightener or straightening tube is used to temporarily straighten the bend during advancement of the device into the pericardial space. In other variations, where the device includes a straight elongate body, a pre-curved device may be used to aid in delivery after proper access has been obtained. In some variations, the suture loop is made from a biodegradable material and is configured to biodegrade after sufficient time has passed to ensure scarring or formation of new tissue that effectively seals of the appendage.

B. Transseptal or Pericardial Access

In the methods described just above, access to the left atrial appendage was obtained both from inside and outside the heart. Of course, the left atrial appendage may be closed off using the systems and devices described here without performing both access procedures as described above. For example, in some variations the methods comprise advancing a first guide having a proximal end and a distal end into the left atrial appendage, through the left atrial appendage, and out of the left atrial appendage, such that one of the proximal or distal ends is within the vasculature, and one of the proximal or distal ends is within the subthoracic space.

Once access has been obtained in this fashion, a closure device may then be advanced into the pericardial space and adjacent to the left atrial appendage, and the left atrial appendage closed off. Of course, the proximal end of the first guide may be within the vasculature, or may be within the subthoracic space. In some variations the closure element is advanced into the pericardial space over the first guide. In other variations, these methods further comprise advancing a second guide into the left atrial appendage, where the second guide comprises an expandable member. The second guide may be advanced to the left atrial appendage over the first guide, though need not be advanced in such a fashion.

Other methods of closing the left atrial appendage without performing both access procedures (i.e., transseptal and epicardial) are also described here. In general, these methods comprise accessing the inside of the left atrial appendage from the epicardial space, using a device that is configured to puncture the appendage wall. An expandable member, such as a balloon, is then advanced through the puncture and into the left atrial appendage and inflated to help position the left atrial appendage while it is being closed off.

Figure 15A:
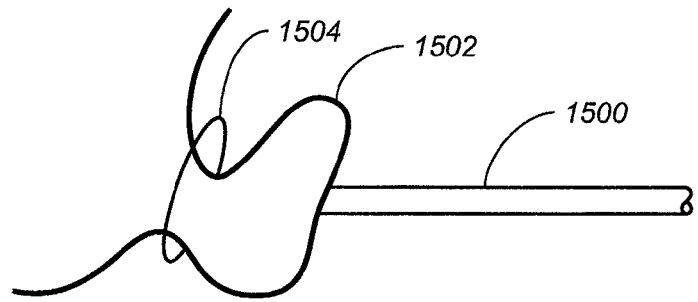
FIGS. 15A-15D depict an alternative illustrative method of closing the left atrial appendage.
Figure 15B:
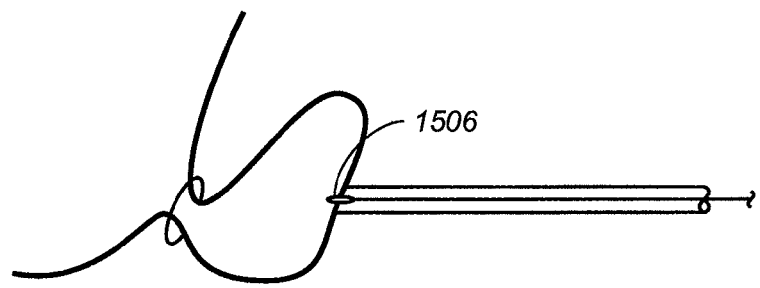
Figure 15C:
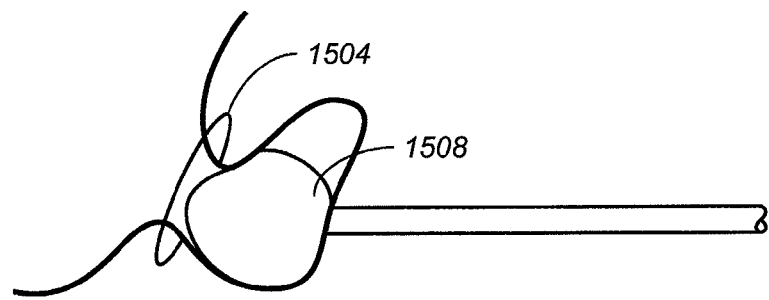
Figure 15D:
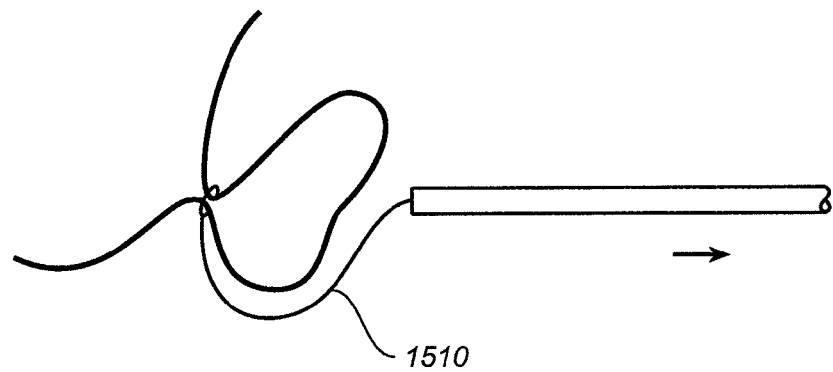
Figure 15E:
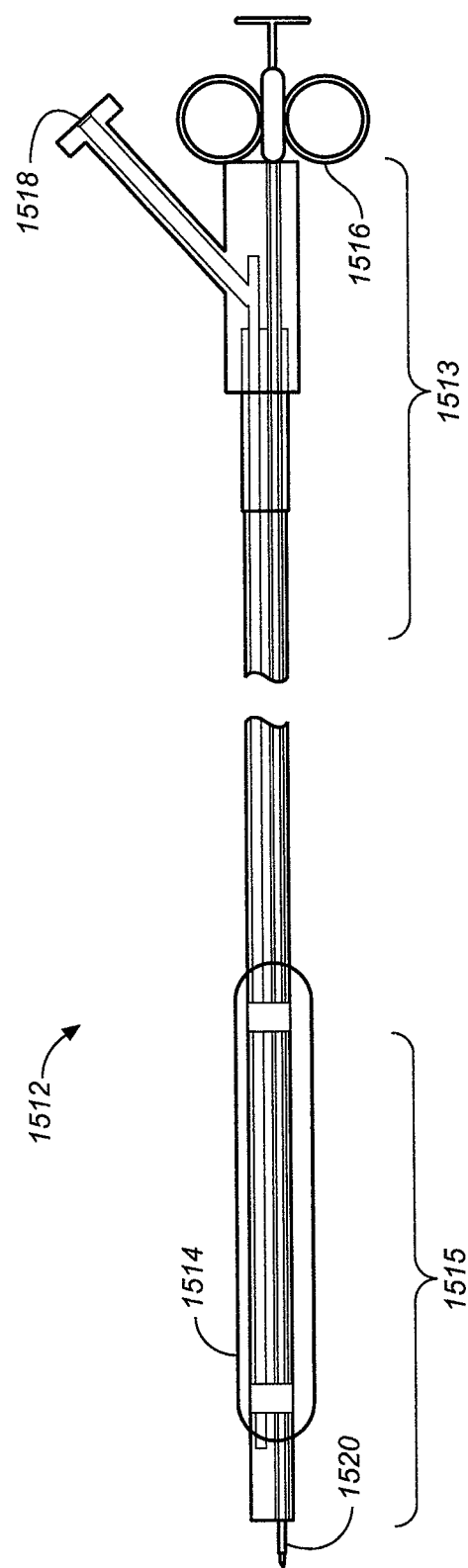
FIG. 15E depicts an illustrative device that may be used to perform the method depicted in FIGS. 15A-15D.

Making reference now to the figures, FIG. 15A shows a left atrial appendage closure device (1500) being advanced adjacent to the left atrial appendage (1502) from the outside of the heart. The closure device may be advanced in any suitable fashion. For example, it may be advanced via a subthoracic approach, or via intercostal or intracostal access, via open surgical access, or the like, as described above. The closure device comprises a closure element (1504) (e.g., a loop as shown in FIG. 15A) that is advanced over the left atrial appendage (1502) and tightened to close off the appendage. The device may comprise a blade or other cutting mechanism (1506), and such mechanism may be used to puncture the left atrial appendage after it has been closed, so that access may be obtained to the inside of the appendage as shown in FIG. 15B. Once access to the inside of the appendage has been obtained, an expandable member (which may be part of the closure device or be a different device meant to cooperate with the closure device) may be expanded within the left atrial appendage for positioning and such as described above. The left atrial appendage may then be closed off again (and confirmed with the visualization techniques described above), and a suture deployed to permanently fix the left atrial appendage in its closed position. The device (1500) may then be withdrawn proximally, and the suture (1510) severed using any of the techniques described above. An illustrative device (1512) for accomplishing this method is shown in FIG. 15E. Shown there is device having a proximal end (1513) and a distal end (1515), balloon (1514), retractable blade (1520), blade actuator (1516), and inflation lumen (1518) for inflating the balloon. Of course other suitable devices may also be used to accomplish this method.

III. Systems

Also described here are systems for closing a left atrial appendage. In general, the systems may comprise a closure device useful for performing a left atrial appendage closure procedure as described above, together with one or more additional components. For example, the system may comprise a first guide having a size and length adapted for accessing the left atrial appendage through the vasculature and comprising an alignment member, a second guide having a size and a length adapted for accessing the pericardial space from a subthoracic region and comprising an alignment member, and a closure device. The alignment member may be any suitable alignment member. For example, the alignment member may comprise radiopaque or echogenic markers, members configured to produce an audible response, one or more interconnecting members, one or more vacuum members, or magnets. In some variations, the alignment members of the first and second guides comprise magnets as shown in FIGS. 13A and 13B respectively.

The closure device may be any of the closure devices described above. For example, the closure device may be one having a closure element that comprises a loop defining a continuous aperture therethrough. The system may further comprise an expandable member or a device comprising an expandable member. The expandable member may be any suitable expandable member, such as, e.g., the balloon catheters described above. The expandable member may have one or more apertures therein for allowing contrast or other fluids to pass therethrough. The system may further comprise a suture loop, and the suture loop may or may not be coupled or couplable to the closure device.

The systems may also comprise one or more devices for severing the suture. Similarly, the systems may also comprise one or more devices for temporarily straightening one or more curves along the elongate body of the closure device. Of course, the device may comprise instructions for using any, all, or a portion of, the system components (e.g., first guide, second guide, closure device, straightening tube, suture cutter, or some combination thereof).

Although the foregoing invention has, for the purposes of clarity and understanding been described in some detail by way of illustration and example, it will be apparent that certain changes and modifications may be practiced, and are intended to fall within the scope of the appended claims.

What we claim is:

1. A method for closing a left atrial appendage of a heart comprising:

advancing a first guide through a vasculature and into the left atrial appendage;

advancing an expandable member into the left atrial appendage;

expanding the expandable member;

advancing a left atrial appendage closure device adjacent to the left atrial appendage from outside the heart, wherein the closure device comprises an elongate body, a closure element comprising a loop, a suture comprising a suture loop, and retention member releasably coupling the closure element and the suture loop, wherein the retention member comprises first and second lumens, wherein the closure element is housed within the first lumen and the suture loop is housed within the second lumen;

closing a neck of the left atrial appendage with the closure element by closing the closure element;

tightening the suture loop to release the suture loop from the retention member after closing the closure element; and leaving the suture loop in place around the left atrial appendage.

2. The method of claim 1, wherein the expandable member comprises a balloon.

3. The method of claim 2, wherein the balloon is echogenic.

4. The method of claim 1, wherein at least a portion of the expandable member has at least one aperture therein.

5. The method of claim 1, further comprising confirming satisfactory closure of the left atrial appendage.

6. The method of claim 1, wherein the first guide, expandable member, closure device, or combination thereof, is advanced under visualization.

7. The method of claim 1, wherein the first guide, expandable member, closure device, or combination thereof, is advanced over a guidewire.

8. The method of claim 1, wherein the suture loop comprises a slip knot.

9. The method of claim 8, wherein the slip knot is a one-way slip knot.

10. The method of claim 1, further comprising severing the suture.

* * * * *